(12) United States Patent
Sugi

(10) Patent No.: US 7,621,910 B2
(45) Date of Patent: Nov. 24, 2009

(54) HIGH FREQUENCY TREATMENT DEVICE HAVING A PAIR OF JAWS WITH ELECTRODES

(75) Inventor: Yoshihiko Sugi, Tokyo (JP)

(73) Assignee: Olympus Corporation (JP)

( * ) Notice: Subject to any disclaimer, the term of this patent is extended or adjusted under 35 U.S.C. 154(b) by 516 days.

(21) Appl. No.: 11/066,646

(22) Filed: Feb. 25, 2005

(65) Prior Publication Data

US 2005/0187547 A1    Aug. 25, 2005

(30) Foreign Application Priority Data

Feb. 25, 2004    (JP)    ............... 2004-050212

(51) Int. Cl.
*A61B 18/14*    (2006.01)
(52) U.S. Cl. .......................... 606/51; 606/48
(58) Field of Classification Search .............. 606/51
See application file for complete search history.

(56) References Cited

U.S. PATENT DOCUMENTS

| | | | |
|---|---|---|---|
| 5,336,222 A | 8/1994 | Durgin, Jr. et al. | ............ 606/50 |
| 5,403,311 A | 4/1995 | Abele et al. | |
| 5,891,142 A * | 4/1999 | Eggers et al. | ................ 606/51 |
| 6,273,887 B1 * | 8/2001 | Yamauchi et al. | ............ 606/48 |
| 6,425,896 B1 * | 7/2002 | Baltschun et al. | ............ 606/51 |
| 6,736,813 B2 * | 5/2004 | Yamauchi et al. | ............ 606/48 |
| 6,767,349 B2 * | 7/2004 | Ouchi | .......................... 606/51 |
| 6,960,210 B2 * | 11/2005 | Lands et al. | .................. 606/50 |
| 2001/0049509 A1 | 12/2001 | Sekine et al. | ............... 604/264 |
| 2003/0114851 A1 | 6/2003 | Truckai et al. | ................ 606/51 |
| 2003/0216733 A1 | 11/2003 | McClurken et al. | .......... 606/51 |
| 2004/0019352 A1 | 1/2004 | Kidooka | ..................... 606/48 |

FOREIGN PATENT DOCUMENTS

| | | |
|---|---|---|
| JP | 2000-70280 | 3/2000 |
| JP | 2001-170069 | 6/2001 |
| WO | WO 02/094341 A2 | 11/2002 |
| WO | WO 02/094341 A3 | 11/2002 |

* cited by examiner

*Primary Examiner*—Lee S Cohen
(74) *Attorney, Agent, or Firm*—Ostrolenk Faber LLP

(57) ABSTRACT

A high frequency treatment device is provided for high-frequency medical treatments including blood stanching. The device comprises an insertion member and a pair of jaws each representing a longitudinal direction, taking on an electrode function along an entire longitudinal region of each jaw, and having a gripping surface. In the device, a link member holds the jaws to be opened and closed in a direction allowing their gripping surfaces to be opposed to each other and links the jaws to a tip of the insertion member to keep electrical insulation between the jaws. An electrical short circuit between the jaws is prevented even when the jaws are mutually closed. A power line applies a high frequency voltage to the jaws via the link member to cause a high frequency current to flow through the jaws. An operation wire transmits open/close movements to the jaws via the link member.

5 Claims, 19 Drawing Sheets

HIGH FREQUENCY TREATMENT DEVICE HAVING A PAIR OF JAWS WITH ELECTRODES

CROSS REFERENCES TO RELATED APPLICATIONS

The present application relates to and incorporates by reference Japanese Patent application No. 2004-050212 filed on Feb. 25, 2004.

BACKGROUND OF THE INVENTION

1. Technical Field of the Invention

The present invention relates to a high frequency treatment device used, for example, with an endoscope for cutting open a portion of tissue of an object to be treated and/or applying a coagulating operation to a portion of tissue of an object to be treated, such as bleeding portion, by supplying high frequency (radio frequency) current to the portion.

2. Related Art

At present, various types of high frequency treatment devices have been proposed, one of which is shown by U.S. Pat. No. 5,403,311. This publication provides a high frequency treatment capable of making high frequency current flow through a bleeding portion for being stanched. This treatment device has an electrode on the tip and supplies high frequency current to the electrode made to touch a bleeding portion. Thus the flow of the current stanches the bleeding portion.

As another conventional example, Japanese Patent Laid-open publication No. 2001-170069 has disclosed a high frequency treatment device, in which the device has a gripper with electrodes. This device is handled to have a bleeding portion gripped by the gripper to which high frequency current is supplied, with the result that a portion of tissue can be cut open and a bleeding portion can be stanched.

Another conventional high frequency treatment device has been proposed Japanese Patent Laid-open publication No. 2000-70280, in which the device has a pair of distal ends of grippers with insulators thereon. In this device of which distal ends are closed to come into contact to each other with the insulators located between the grippers. Thus the insulators make conductive gripping surfaces of the grippers prevent from being directly touched with each other, so that electric short circuit between the grippers can surely be avoided when the grippers are closed.

Of the above conventional references, the high frequency treatment device typical of the device shown in U.S. Pat. No. 5,403,311 is able to simply stanch a diseased part, because it is sufficient to supply current to the electrode touched to the diseased part. This is advantageous when urgent medical treatments are required, but disadvantageous in that this device may be difficult to stop projectile bleeding due to a lack of sufficient press of the electrode onto the diseased part. That is, simply pressing the electrode onto the diseased part results in an insufficient press to blood stanching.

Further, the high frequency treatment device represented by Japanese Patent Laid-open publication No. 2001-170069 can fully press a diseased part by the gripper and, under such a grip, high frequency current is supplied to the electrodes for blood stanching. This gripping technique is very useful for stopping projectile blooding. However, to grip a portion of tissue of an object to be treated in a quick and precise manner requires surgeon's relatively complicated operations. This means that this kind of device is not suitable for urgent medical treatments.

In addition, the device proposed by Japanese Patent Laid-open publication No. 2000-70280 is still useful, because, with a diseased part pressed sufficiently by the gripper, high frequency current is made to flow through the electrodes for blood stanching. Concurrently, with jaws of the grippers made to close to each other, a side of the gripper can be pressed onto a diseased part and high frequency current is fed to the electrodes to stop bleeding easily. However, due to the fact that the insulators on the gripper are nothing to do with current flow, there are some limitations on effective positions to grip the tissue and press the gripper onto the tissue. Precisely, it is always necessary to pay attention to which part of the gripping surfaces should be used for gripping and which part of the gripper should be used for pressing.

SUMMARY OF THE INVENTION

Accordingly, the present invention provides a high frequency treatment device which is easy to use for both gripping and pressing operations.

According to one aspect, the present invention provides a high frequency treatment device comprising: an insertion member; a pair of jaws each representing a longitudinal direction, taking on an electrode function along an entire region of each jaw in the longitudinal direction, and having a gripping surface; a link member holding the pair of jaws to be opened and closed in a direction allowing the gripping surfaces of the jaws to be opposed to each other and linking the pair of jaws to a tip of the insertion member in a condition in which an electrical insulation between the jaws is kept; a short-circuit preventing member preventing an electrical short circuit between the jaws when the jaws are closed to each other; a power line being disposed through the insertion member and applying a high frequency (radio-frequency) voltage to the jaws via the link member to cause a high frequency current to flow through the jaws; and an operation wire being disposed through the insertion member and transmitting open/close movements to the jaws via the link member.

Preferably, at least one of the paired jaws comprises an electrically insulative jaw body; and positive and negative electrodes serving as the electrode function by receiving an application of the high frequency voltage and being disposed through an entire region on an outer surface of each jaw body in the longitudinal direction.

According to another aspect, the present invention provides a high frequency treatment device comprising: an insertion member insertable into a body of an object to be examined; a pair of jaws being disposed at a tip of the insertion member and consisting of a first and second jaws gripping a portion of tissue to be treated of the object; and a handle coupled with a base of the insertion member and used for opening and closing the jaws, wherein each of the first and second jaws has a gripping surface used for the gripping, a back surface located back to back to the gripping surface, a first and second side surfaces each connecting the back surface and the gripping surface, and one or more pairs of positive and negative electrodes, wherein both of the positive and negative electrodes are exposed on the back surface of each of he first and second jaws, at least one of both the positive and negative electrodes is exposed, at least one in number, on the gripping surface of the first jaw, at least one of both the positive and negative electrodes is exposed, at least one in number, on the first and second side surfaces of the first jaw, at least one electrode opposite in polarity to the electrodes exposed on the gripping surface of the fist jaw is exposed on the griping surface of the second jaw, and at least one electrode opposite in polarity to the electrodes exposed on the first and second side surfaces of the first jaw is exposed on the first and second side surfaces of the second jaw.

In the present invention and the following embodiments, the terms "positive" and "negative" are made reference to the electrode members to which high frequency (radio frequency) voltage is applied to supply high frequency current for medical high frequency treatments, for it is occasionally necessary to distinguish the two types of electrode members from one the other. The "positive" polarity corresponds to a non-grounded electrode member and the "negative" polarity corresponds to a grounded electrode member.

DETAILED DESCRIPTION OF THE PREFERRED EMBODIMENTS

In connection with the accompanying drawings, various embodiments of the present invention will now be described.

First Embodiment

Referring to FIGS. 1-8, a first embodiment of a high frequency (radio-frequency) treatment device (also called diathermy treatment device) according to the present invention will now be described.

Figure 1:
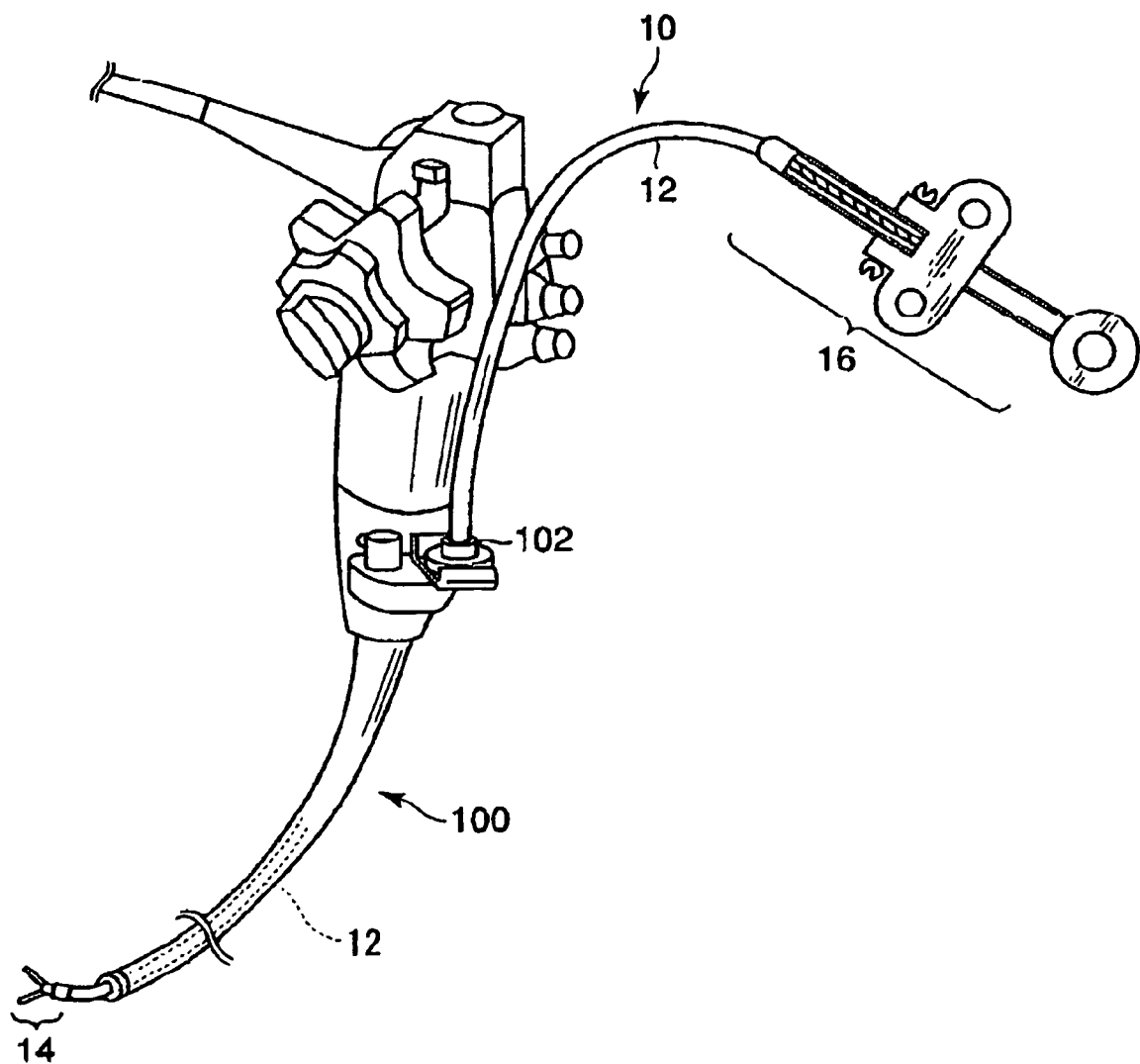
FIG. 1 is a perspective view conceptually showing an endoscope with an insertion channel through which a bipolar forceps functioning as a high frequency treatment device according to a first embodiment of the present invention.

As shown in FIG. 1, a bipolar forceps (bipolar diathermy forceps) 10 (serving as a high frequency treatment device) according to the present embodiment is provided for cutting open and coagulating a portion of tissue of an object to be treated. This bipolar forceps 10 are used with, for example, an endoscope 100, with the forceps 10 inserted through an insertion channel of the endoscope 100.

The bipolar forceps 10 are equipped with a flexible insertion member 12 formed into a thin and long tubular shape whose both ends are respectively referred to as a tip and a base, a treatment member 14 rigidly secured to the tip of the insertion member 12, and a handle 16 formed at the base of the insertion member 12 and configured to operate the treatment member 14.

Figure 2A:
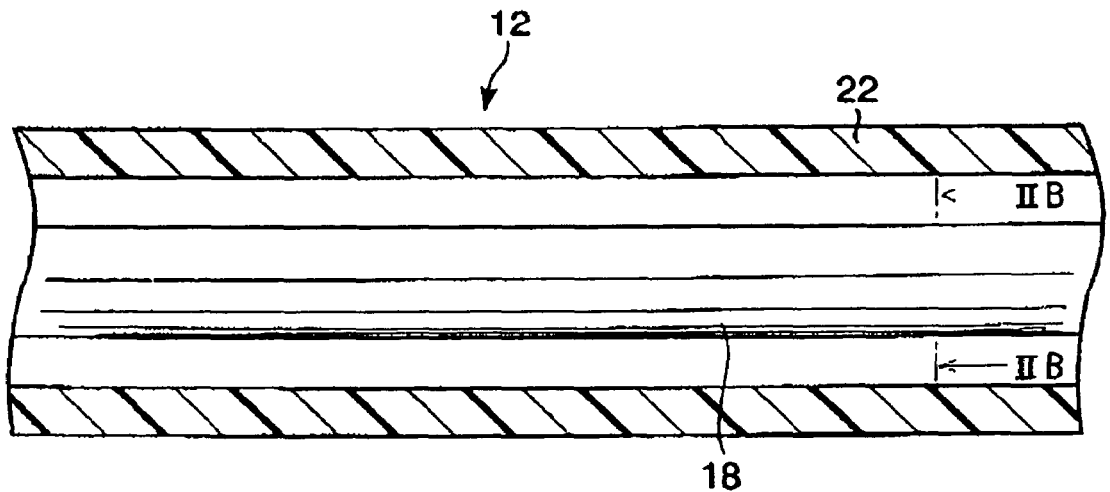
FIG. 2A is a partial section, which is taken along a line IIB-IIB, outlining an insertion member of the bipolar forceps in the first embodiment.

As shown in FIG. 2A, between the treatment member 14 and the handle 16, a conductive wire 18 for conveying operational movements and currying current is movably inserted into the insertion member 12 along an axial direction thereof. The wire 18 therefore connects the treatment member 14 and the handle 16. The wire 18 conveys operational movements from the handle 16 to the treatment member 14 and carries high frequency current from the handle 16 to the treatment member 14.

The insertion member 12 is provided with a sheath 22 rotatable against the treatment member 12. The sheath 22 is made from a resin material that exhibits an excellent flexibility. The sheath 22 may however be formed from a metal-made flexible coil, not limited to the resin materials. The outer diameter of the sheath 22 is 1 to 6 mm. Particularly it is preferable if the diameter is 1.8-3.6 mm, because of a higher insertion performance along an insertion channel 102 of the endoscope 100. In an inner bore of this sheath 22, the foregoing wire 18 is movably arranged along the axial direction of the sheath 22.

Figure 3A:
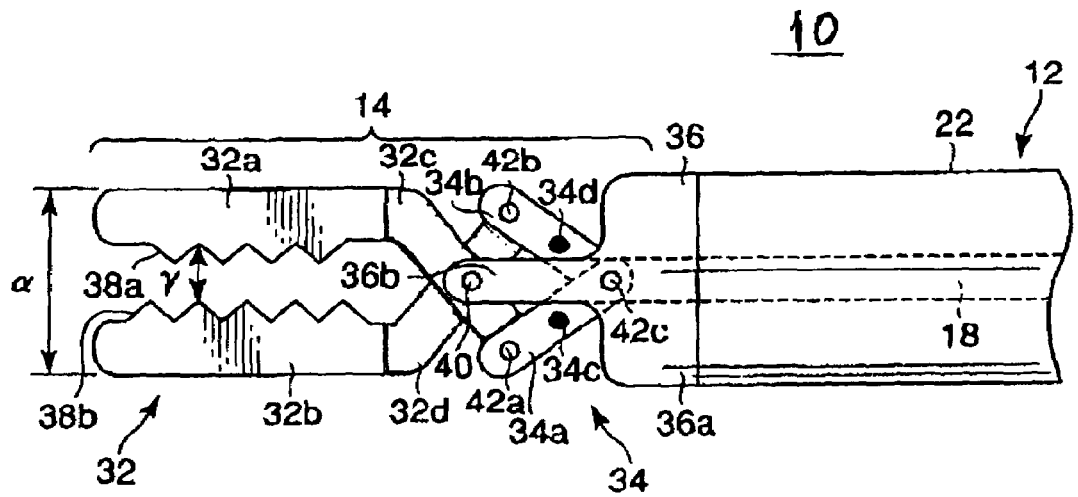
FIG. 3A is a side view outlining a treatment member disposed at a tip of the bipolar forceps in the first embodiment, the treatment member being able to take a closed position as shown therein.
Figure 3B:
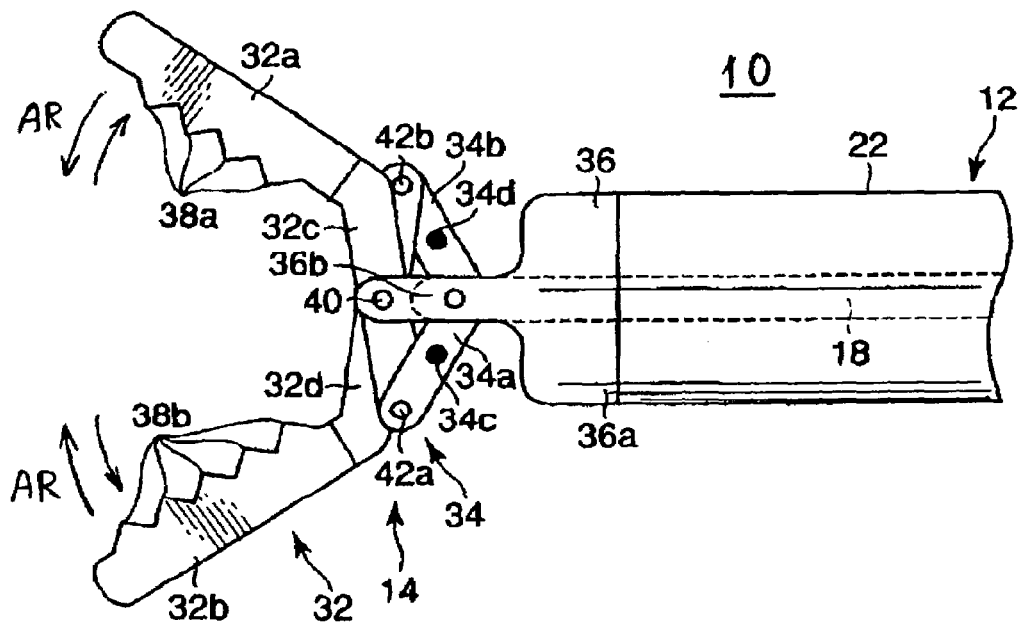
FIG. 3B is the side view of the treatment member shown in FIG. 3A, the treatment device being able to take an open position as shown therein.

As shown in FIGS. 3A and 3B, the treatment member 14 is equipped with a gripper (grasper) 32 openable and closable in order to grip (grasp) tissue, a link mechanism 34 making the gripper 32 open and close, and a tip securing member 36 which is hard and arranged at the tip of the insertion member 12. Of these, the tip securing member 36, which has an approximately tubular shape, is provided with a tubular member 36a coupled with the tip of the sheath 22 and a pair of arms 36b rigidly formed with the tubular member 36a and elongated forwardly from the tubular member 36a. The pair of arms 36b holds both ends of a pin 40, with which coupling members 32c and 32d of jaws 32a and 32b described later are held rotatably around the pin 40. The outer surfaces of the tubular member 36a and arms 36b are coated with insulative material such as fluorocarbon resin.

The gripper 32 is provided with a pair of jaws 32a and 32b each having a gripping surface 38a (38b) and joints 32c and 32d formed as base portions of the respective jaws 32a and 32b. Each of the jaws 32a and 32b is integrated with each of the joints 32c and 32d each made from a hard conductive member. As understood from the FIGS. 3A and 3B, each of the joints 32c and 32d forms the base portion of each jaw 32a (32b), but arranged to be bent at a predetermine angle made from a longitudinal axis of each jaw 32a (32b). The joints 32c and 32d are respectively bent from the jaws 32a and 32b so as to be crossed with each other. This crossing structure allows the gripping surfaces 38a and 38b to be located face to face when the gripper 32 is closed as shown in FIG. 3A (hereinafter, the jaw positions shown in FIG. 3A are referred to as "closed," in contrast, jaw positions shown in FIG. 33 are referred to as "open.")

In the present embodiment, the jaws 32a and 32b function as gripping members which are able to grip a portion of tissue of a patient and function as electrodes to make high frequency current pass through the gripped tissue. As described above, a side of each of the jaws 32a and 32b is formed to provide the gripping surface 38a (38b) which is made to touch the tissue to be gripped. Each of the gripping surfaces 38a and 38b has irregularities to enhance a gripping force. The side-view shapes of the irregularities are for example triangular as shown in FIGS. 3A and 3B, but this is not a decisive shape. Any shapes, such as round shapes and quadrangular shapes, can be applied too the irregularities. The surface, including the gripping surface 38a (38b), of each jaw 32a (32b) is entirely subjected to thin coating of, for example, a fluorocarbon resin for preventing the tissue from being burned dry to the jaws 32a and 32b.

The outer surfaces of the joints 32c and 32d of the gripper 32 are formed into insulative surfaces. That is, the joints 32c and 32d, which compose bases of the respective jaws 32a and 32b, are coated with insulative material, so that an electric short circuit between the joints 32c and 32d touched to each other is surely prevented. The insulative outer surfaces of the joints 32c and 32d can be formed by covering the entire joints 32c and 32d with an electrical insulative sheet or can be coated with insulative material.

The joints 32c and 32d, which compose the bases of the pair of jaws 32a and 32b, are crossed to each other and rotatably held by a pin 40 bridging the tips of the arms 36b of the tip securing member 36. Thus the pair of jaws 32a and 32b can be opened and closed mutually as shown by arrows AR in FIGS. 3B (opened position) and 3A (closed position) around the pin 40 serving as a fulcrum at the tips of the arms 36b. The pin 40 is coated with insulative material such as fluorocarbon resin.

A distance (width) α between the outer surfaces of the jaws 32a and 32b measured when the pair of jaws 32a and 32b is closed (at the mutually nearest positions) is 1.5 to 6 mm in the present embodiment. Especially it is preferable that the distance α is 2 to 3.5 mm. This distance α is set to establish both the insertion performance into the endoscope's insertion channel 102 and an appropriate region for blood stanching.

The axial length of each of the jaws 32a and 32b is in a range of 1 to 20 mm, and particularly, the axial length of 4 to 12 mm is preferable. This length is also determined to have both the insertion performance into the endoscope's insertion channel 102 and an appropriate region for blood stanching.

The link member 14 is provided with a first and second links 34a and 34b. One end of the first link 34a is rotatably coupled with the base of the joint 32c for one of the jaws, 32a, with the aid of a first rotatably support pin 42a. Further, one end of the second link 34b is rotatably coupled with the base of the joint 32d for the other of the jaws, 32b, with the aid of a second rotatably support pin 42b. The other ends of both first and second links 34a and 34b are rotatably held by a third rotatably support pin 42c at the tip of the wire 18. In short, in the link mechanism 34, the pair of links 34a and 34b are arranged to rotatably connect to the tip of the wire 18 the help of the third rotatably support pin 42c. Thus, in response to pushing and pulling the wire, the first and second links 34a and 34b ban be rotated around the third rotatably support pin 42c. The rotations of the links 34a an 34b make it possible that the bases of the jaws 32a and 32b rotate around the first and second rotatably support pins 42a and 42b, respectively. The jaws 32 and 32b can therefore be rotated around the pin 40 in the mutually opposite directions as shown by arrows AR in FIG. 3B.

Since the first and second links 34a and 34b are also coated with insulative material such as fluorocarbon resin, respectively, so that an electrical short-circuit between the links 34a and 34b can be prevented. The third rotatably support pin 42c is also subjected to insulative coating with material such as fluorocarbon resin. Thus an electrical separation between the third rotatbly support pin 42c and the arms 36b are secured, with no conductive linkage therebetween.

As shown in FIGS. 3A and 3B, the links 34a and 34b have stoppers 34c and 34d to restrict angular rotation amounts of the jaws 32a and 32b, respectively. Each of the stoppers 34c and 34d is disposed on each of sides of the links 34a and 34b to protrude therefrom. The stoppers 34c and 34d are located in such a manner that, when the wire 18 is pulled by an operator to establish a gap (spacing) of predetermined distance γ between the jaws 32a and 32b, the stoppers 34a and 34b just come into contact with the arms 36b, respectively. The stoppers 34c and 34d may have any outer shapes, not limited to a cylindrical shape as depicted in FIGS. 3A and 3B. Any outer shapes including a triangle and a square may be available for the stoppers 34c and 34d.

It is therefore possible to prevent the gripping surfaces 38a and 38b of the respective jaws 32a and 32b from being touched to each other, even when an operation to maximally close the jaws 32a and 32b is applied to the handle 16 (i.e., even when the jaws 32a and 32b have the closest distance γtherebetween, as shown in FIG. 3A). Thus no electrical short-circuit will be caused between the jaws 32a and 32b. In terms of sustaining an appropriate gripping force, the distance γ is preferably a value ranging from 0.1 mm to 2 mm.

Figure 4:
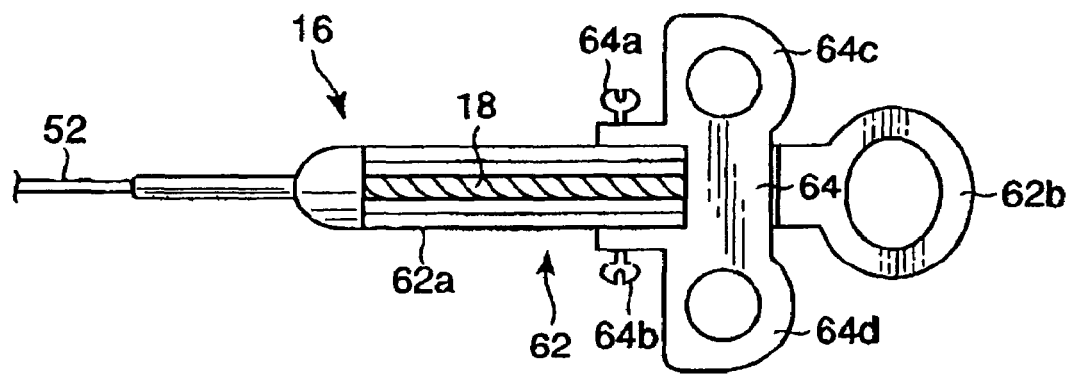
FIG. 4 is a side view outlining a handle disposed at a base end of the bipolar forceps in the first embodiment.

As shown in FIG. 4, the handle 16 is provided with an operating main body 62 and a slider 64. The operating main body 62 includes a shaft-like sliding guide 62a and a finger-hooked ring 62b disposed at the base of the sliding guide 62a. The slider 64, which is slidable along the sliding guide 62a, comprises first and second current-conducting connectors 64a and 64b. The slider 64 further comprises finger-hooked rings 64c and 64d with which the index and middle fingers are hooked. The wire 18 is inserted in the sheath 22 of the insertion member 12 to extend therealong and the base of the wire 18 is connected to the first and second current-conducting connectors 64a and 64b disposed on the slider 64, respectively. The connectors 64a and 64b each are coupled with cables coming from a high frequency cautery power supply unit (not shown). This power supply unit is switched on/off by, for example, operating a foot switch coupled thereto and configured to generate high frequency voltage.

The slider 64 is moved to slide along the sliding guide 62a, which makes the wire 18 to slide backward and forward. Those slide movements cause the jaws 32a and 32b at the tip of the treatment member 14 to open and close, line shown in FIGS. 3A and 3B.

Figure 2B:
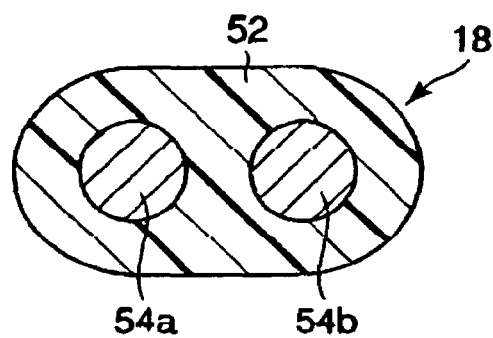
FIG. 2B is a section, which is taken along a line IIB-IIB in FIG. 2A, showing a conductive wire in FIG. 2A.

As shown in FIG. 2B, the wire 18 comprises an insulative coating member 52 of high insulation performance, which is made from fluorocarbon resin or polyolefin, and a pair of conductive wires 54a and 54b mutually insulated by the coating member 52. It is also possible to have the two conductive wires 54a and 54b inserted into insulative tubes with two or more lumens. Alternatively, the two conductive wires 54a and 54b may be covered by insulative coats, respectively. Still, the conductive wires 54a and 54b may not be confined to the forgoing structure in which the two wires are combined into one cable shown in FIG. 2B, but the wires 54 and 54b may be separated as independent cables.

Of the two conductive wires 54a and 54b, the first conductive one 54a has a tip coupled with the first link 34a by the third rotatably support pin 42c (refer to FIG. 3A). In contrast, the base of the first conductive wire 54a is coupled with the first current-conducting connector 64a. On the other hand, the second conductive wire 54b has tip linked with the second link 34b by the third rotatably support pin 42c. The base of the second conductive wire 54b is connected with the second current-conducting connector 64b.

To the third rotatably support pin 42c are connected with the wire 18 and both the first and second conductive wires 54a and 54b, in which the conductive wires 54a and 54b are electrically separated from each other. Though not shown, the third rotatably support pin 42c is formed of a pair of conductive members between which an insulator is placed. Precisely, the pin 42c is formed into a bar consisting of a pair of conducting portions and an insulator bridging both conducting portions. To the conducting portions are connected with the forgoing first and second conductive wires 54a and 54b. One pair of conducive portions of the pin 42c has linkages with the first and second links 34a and 34b, respectively.

Accordingly, all of the first current-conducting connector 64a, the first conductive wire 54a of the wire 18, the third rotatably support pin 42c, the first link 34a, the first rotatably support pin 42a, and the first jaw 32a are not only eclectically connected but also mechanically coupled with each other. By contrast, all of the second current-conducting connector 64b, the second conductive wire 54b of the wire 18, the third rotatably support pin 42c the second link 34b, the second rotatably support pin 42b, and the second jaw 32b are not only eclectically connected but also mechanically coupled with each other.

The operations and advantages of the cutting-open/coagulating bipolar forceps 10 according to the present embodiment will now be explained.

First, one ends of not-shown cables are connected respectively to the first and second current-conducting connectors 64a and 64b of the bipolar forceps 10. The other end of each of the cables is connected with the high frequency coutery power supply unit not shown, thus establishing the connections between the bipolar forceps 10 and the high frequency coutery power supply unit.

An operator grips the handle 16 such that the thumb is put in the finger-hooked ring 62b of the operating main body 62 and the first and middle fingers are put in the finger-hooked rings 64c and 64d of the slider 64. Thus the operator can pull the slider 64 to move it along the slicing guide 62a. This pulling operation causes the wire 18 to be pulled back toward the base side, the wire 18 being connected to the first and second current-conducting connectors 64a and 64b as well as the slider 64. Responsively, the tip of the wire 18 is forcibly moved back to the base side, with tip securing member 36 fixed. This will cause the third rotatably support pin 42c to be pulled back as well.

In response to a movement of the third rotatably support pin 42c, both tips of the first and second links 34a and 34b are pulled back, which will cause both the links 34a and 34b to rotate about the third rotatably support pin 42c. The rotation of the links 34a and 34b involves pulling of the first and second rotatably support pins 42a and 42b backward, so that the pair of joints 32c and 32d is rotated bout the pin 40. This will cause the pair of jaws 32a and 32b to approach to each other, that is, to close, as shown in FIG. 3A.

When this close position of the bipolar forceps 10 is completed, the insertion member 12 thereof is inserted into the insertion channel 102 of the endoscope 100, as shown in FIG. 1, so that the insertion member 12 is inserted into the body of a patient. Then the endoscope 100 is operated to guide the treatment member 14 at the tip of the insertion member 12 to a spatial position near a tissue to be treated in the body.

When the treatment member 14 is positioned near the tissue, the slider 64 of the handle 16 is operated by an operator to slide forward along the sliding guide 62a. This operation allows the wire 18 to advance, which will give the operations to the jaws, which are opposite to the above. In other words, the link member 34 is forced to drive the jaws 32a and 32b to separate from each other, resulting in the open position of the jaws, as shown in FIG. 3B.

Figure 5:
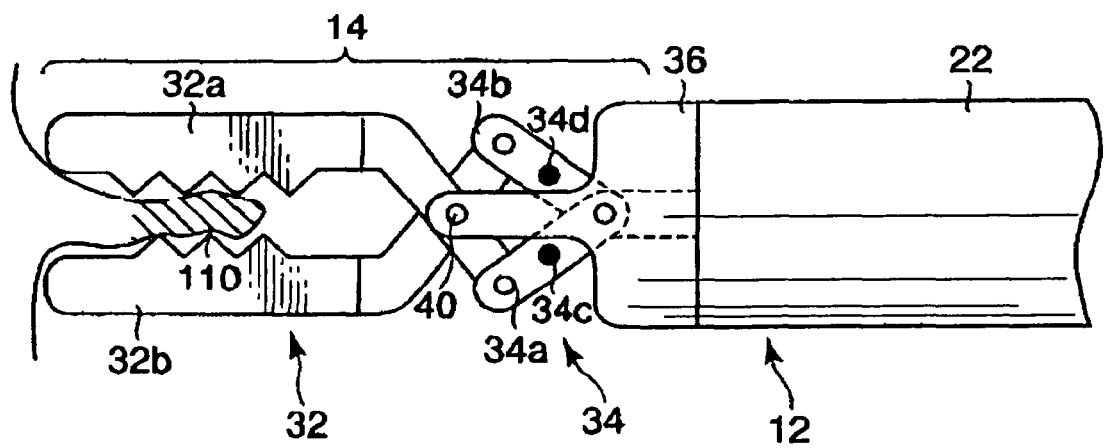
FIG. 5 is a side view conceptually showing a state in which the treatment of the bipolar forceps according to the first embodiment grips tissue of an object to be examined.

Then the jaws 32a and 32b, which are in their open attitude, are moved to bite at a portion of the tissue 110 to be treated, with the tissue 110 between the jaws 32a and 32b. The slider 64 is then operated to close jaws 32a and 32b. That is, as shown in FIG. 5, the tissue 110 to be treated is gripped by the jaws 32a and 32b, with the gripping surfaces 38a and 38b facing the tissue 110 respectively.

The not-shown foot switch connected to the high frequency cautery power supply unit is operated to apply high frequency voltage to the first and second current-conducting connectors 64a and 64b through cables. The voltage is therefore supplied to the jaw 32a via the connector 64a, the first conductive wire 54a of the wire 18, the third rotatably support pin 42c, the first link 34a, and the first rotatably support pin 42a. Like this, the voltage is supplied to the jaw 32b via the connector 64a, the first conductive wire 54b of the wire 18, the third rotatable support pin 42c, the second link 34b, and the second rotatably support pin 42b. Thus high frequency current is caused to pass between the pair of jaws 32a and 32b, i.e., through the tissue 110 gripped by the electrodes (i.e., jaws 32a and 32b), resulting in that the tissue 110 coagulates due to heat caused by the high frequency current.

In this coagulating operation, if the tissue 110 to be treated is thin, the jaws 32a and 32b are prevented from being short-circuited when the high frequency current is supplied to the jaws 32a and 32b, because there is formed a gap γ between the gripping surfaces 38a and 38b and the outer surfaces of the joints 32c and 32d are kept insulative. The minimum gap γ between the gripping surfaces 38a and 38b is secured by touching the arm 36b of the tip securing member 36 to the stoppers 34c and 34d. The stoppers 34c and 34d limit the slider 64 from moving backward any more, even if the operator wants. Additionally, because there is no insulative portion on the gripping surfaces 38a and 38b of the jaws 32a and 32b, there is no need for worrying about positions on the clipping surfaces 38a and 38b at which the tissue 110 is gripped.

Figure 6:
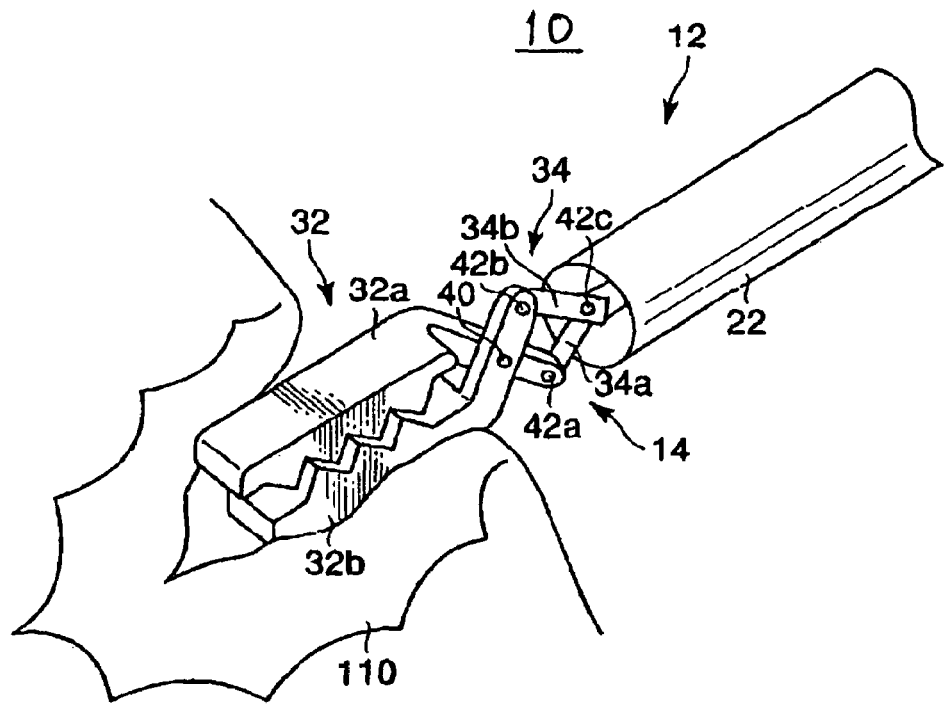
FIG. 6 is a perspective view conceptually explaining a state in which the treatment of the forceps according to the first embodiment cuts open the tissue.

Additionally, with the jaws 32a and 32b gripping a portion the tissue 110, the tissue 110 can also be cut open by supplying the high frequency current to the jaws 32a and 32b, as shown in FIG. 6. In this cutting open operation, since the jaws 32a and 32b are subjected to the non-stick coated layer, the electrical short circuit resulting from clagged mucosa of the tissue to the jaws 32a and 32b can be prevented between the jaws 32a and 32b.

Figure 7:
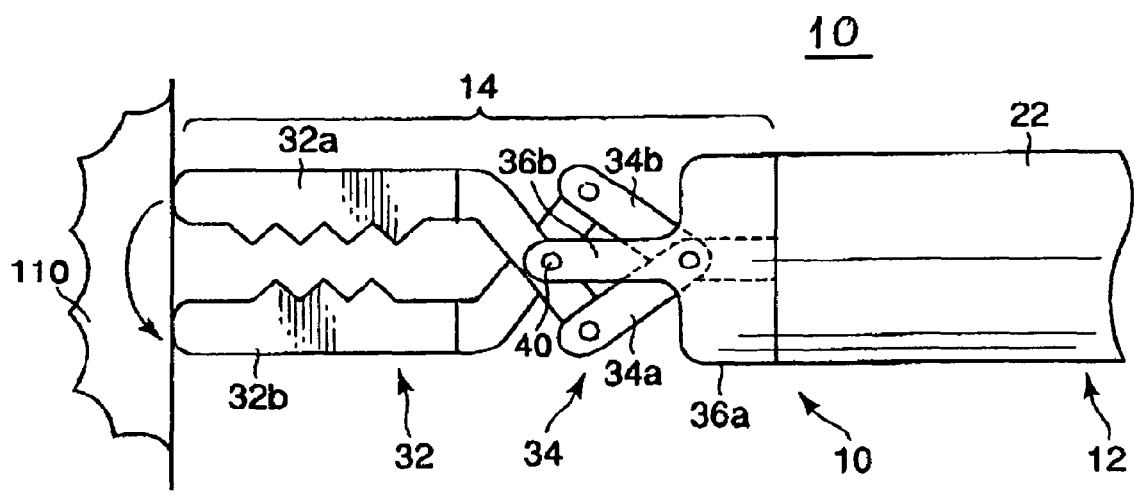
FIG. 7 is a side view explaining a state in which the treatment member of the bipolar forceps according to the fist embodiment is made to touch the tissue.

Meanwhile, it is sometimes desired to simply apply a blood stanching operation to tissue 110, without gripping it. For doing this, as shown in FIG. 7, the front surfaces of the respective jaws 32a and 32b are made to press onto a treatment-desired portion of the tissue 110. With this pressed state kept, the jaws 32a and 32b receives high frequency current supply as stated above, whereby the desired portion of the tissue 110 coagulates simply for stop bleeding due heat caused by the current. This operation also enjoys the benefit of the minimum gap γ formed between the jaws 32a and 32b. That is, the gap γ prevents the jaws 32a and 32b from being short-circuited with each other, while still making the high frequency current pass through the tissue 110. In this way, the tissue 110 can undergo the coagulating treatment for stop blooding in a simple manner.

Figure 8:
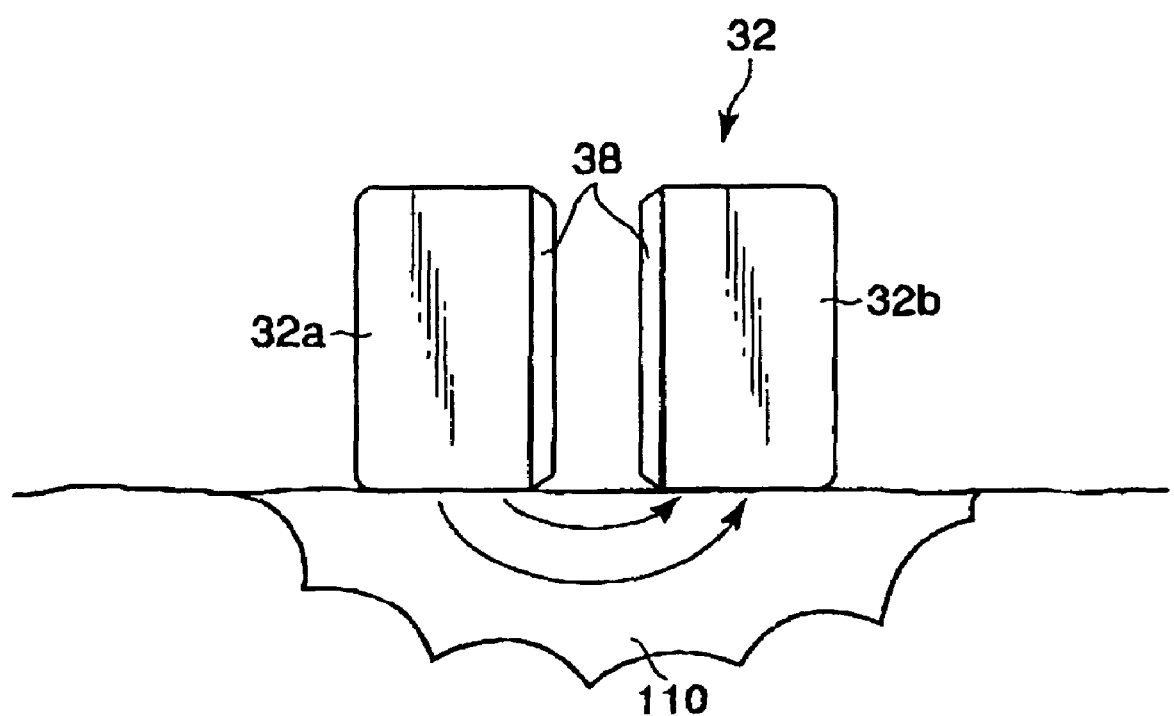
FIG. 8 is a frontal view explaining a state in which the treatment member of the bipolar forceps according to the fist embodiment is made to touch the tissue.

An alternative stop bleeding operation is to make flat side surfaces of the respective jaws 32a and 32b press onto a desired portion of tissue 110, as shown in FIG. 8. With the attitudes of the jaws 32a and 32b kept as shown in FIG. 8, the high frequency current is supplied to the jaws 32a and 32b by applying the high frequency voltage, resulting in coagulating the pressed portion of the tissue 110 for blood stanching. In this operation, the short circuit between the jaws 32a and 32b is prevented well due to the minimum gap γ between the jaws 32a and 32b and the insulative outer surfaces of the joints 32c and 32d, whilst the current flow through the tissue 110 is secured. Thus the tissue 110 can be coagulated at its desired portion, for stop bleeding in a simple but steady manner.

As described so far, the present embodiment can provide various advantages.

First, the predetermined-length gap γ is formed between the jaws 32a and 32b and the joins 32c and 32d have the insulative outer surfaces. These structures prevent the short circuit between the jaws 32a and 32b when the jaws 32a and 32b are closed to each other.

Secondly, supplying the high frequency current to the jaws 32a and 32b gripping a desired portion of tissue 110 between their gripping surfaces 38a and 38b allows the portion to be coagulated for stop bleeding. Moreover, pressing the mutually closed jaws 32a and 32b onto a desired portion of tissue 110 and supplying the high frequency current to the jaws 32a and 32b result in blood stanching. In this blood stanching, there is no the directionality of the jaws 32a and 32b, which means that the front surfaces and any side surfaces of the jaws can be used to be pressed for the blood stanching operation. It is therefore, unlike the conventional, to cope with various kinds of bleeding states of the tissue. Namely, it is possible to provide the bipolar forceps 10 with the openable/closable gripper 32 which has the capability of gripping a desired portion of the tissue and being pressed onto (made to touch) a desired portion of the tissue without paying attention to pressing portions of the gripper 32. As a result, various types of high frequency medial treatments can be done in an easier manner.

Differently from the conventional, there are no insulation portions on the jaws 32a and 32b. Thus there is no need to select which part of the jaws 32a and 32b should be used for gripping or touching (being pressed onto) a desired portion of the tissue. The time necessary for the treatments can therefore be shortened.

Second Embodiment

Figure 9A:
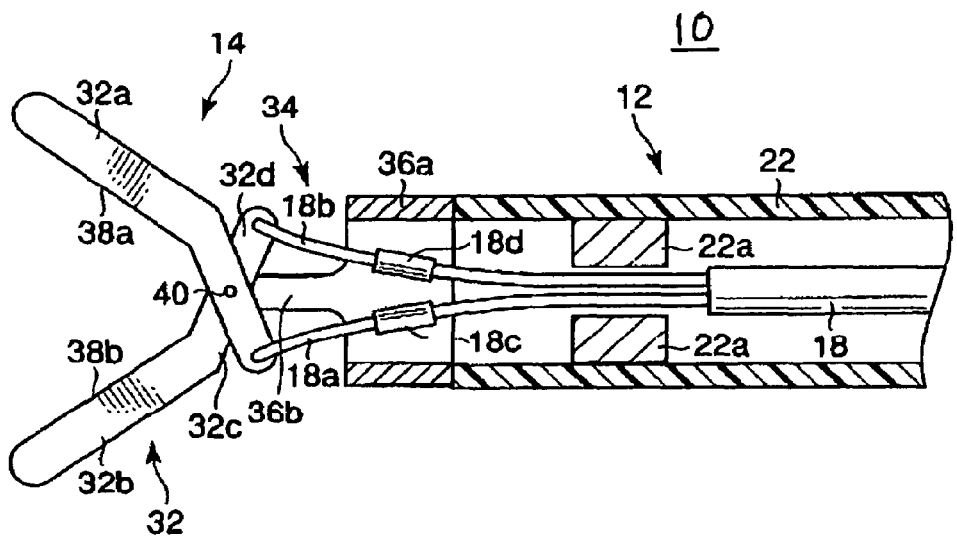
FIG. 9A is a partly sectioned side view outlining a treatment member disposed at a tip of a bipolar forceps serving as the high frequency treatment device in a second embodiment of the present invention, the treatment member being able to take an open position as shown therein.
Figure 9B:
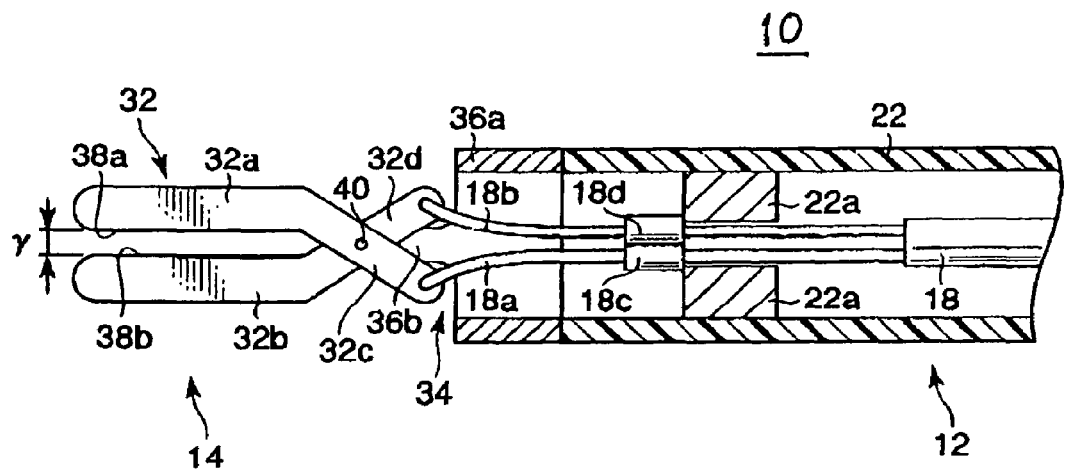
FIG. 9B is the partly sectioned side view outlining the treatment member shown in FIG. 9A, the treatment member being able to take a closed position as shown therein.

Referring to FIGS. 9A and 9B, a second embodiment of the high frequency treatment device according to the present invention will now be described. Incidentally, for the sake of simplified explanations, the similar or identical parts in the present and subsequent embodiments to those in the first embodiment will have the same reference numerals.

The second embodiment corresponds to a modification of the bipolar forces 10 explained in the first embodiment. To be specific, there is provided another example of sustaining the minimum gap γ between the jaws 32a and 32b (precisely, between the gripping surfaces 38a and 38b) when the jaws 32a and 32b are closed. The bipolar forceps 10 according to the present embodiment has a link mechanism 34 different in structures from that explained in the first embodiment.

As shown in FIG. 9A, the tip of the wire 18 is divided into two so as to connect to first and second branch wires 18a and 18b which are conductive. The first branch wire 18a is connected to the first conducive wire 54a (refer to FIG. 2A), whereas the second branch wire 18b is connected to the second conductive wire 54b. The tips of the first and second wires 18a and 18b are coupled respectively with the joints 32c and 32d functioning as the bases of the jaws 32a and 32b so as to allow the joints 32c and 32d to rotate around the pin 40. The wires 18a and 18b have outer surfaces on each of which an insulative layer is coated. First and second stoppers 18c and 18d are fixed at axial predetermined positions of the first and second branch wires 18a and 18b, respectively. The positions are decided appropriately to touch a blocker 22a formed on the inner wall surface of the sheath 22, when the wire 18 is pulled back.

The blocker 22 is positioned at an axial predetermined position of the sheath 22 and formed into a cylinder having a bore through which the two branch wires 18a and 18b are placed movably in the axial direction of the insertion member 12. However, the shapes of the first and second stoppers 18c and 18d and the blocker 22a are not limited to those shown in FIGS. 9A and 9B. Any shapes can be used as long as the equivalent functions are achieved.

As shown in FIG. 9B, the positional relationship of the first and second stoppers 18c and 18d and the blocker 22a is designed such that the first and second stoppers 18c and 18d are just made to touch the blocker 22a, when the distance (spacing) between the gripping surfaces 38a and 38b of the jaws 32a and 32b is reduced down to a predetermined minimum length γ in response to pulling the wire 18 backward. Hence it is no longer possible for an operator to pull back the slider 64, when such a contact between the first and second stoppers 18c and 18d and the blocker 22a is once established. The minimum gap length γ is therefore secured between the jaws 32a and 32b of the treatment member 14.

As a variation, both the length of the wire 18 and the sliding guide 62a of the operating main body 62 can be adjusted so that, when the predetermined length γ is established between the gripping surfaces 38a and 38b of the jaws 32a and 32b, the slider 64 is located nearest to the operating main body 62 so as not to permit the move of the slider 64 backward any more.

The operations of the bipolar forceps 10 according to the present embodiment will now be described.

The handle 16 shown in FIG. 4 is operated by an operator so that the wire 18 is moved forward and backward along the sheath 22 of the insertion member 12. This operations are converted into forward and backward movements of the first and second branch wires 18a and 18b, which are then transmitted to the joints 32c and 32d. The jaws 32a and 32b are then operated around the pin 40 so that the jaws 32a and 32b get separated from each other or closer with each other (i.e., open and close).

That is, an operator's forward operation of the wire 18 enables the jaws 32a and 32b to open, while an operator's backward operation of the wire 18 results in the close of the jaws 32a and 32b. In this closing operation, the distance between the gripping surfaces 38a and 38b is gradually reduced, and finally becomes the predetermined value γ just when the first and second stoppers 18c and 18d are made to touch the block 22a for a stop thereat. The wire 18 cannot be pulled backward any more, with the result that the minimum distance γ between the gripping surfaces 38a and 38b can be kept.

As understood from the above, the bipolar forceps 10 according to the present embodiment can enjoy the identical advantages to those explained in the first embodiment. Additionally, the choice in design can be expanded.

Third Embodiment

Referring to FIGS. 10A and 10B to 13, a third embodiment of the present embodiment will now be described. This embodiment relates to another structure of the jaws.

Figure 10A:
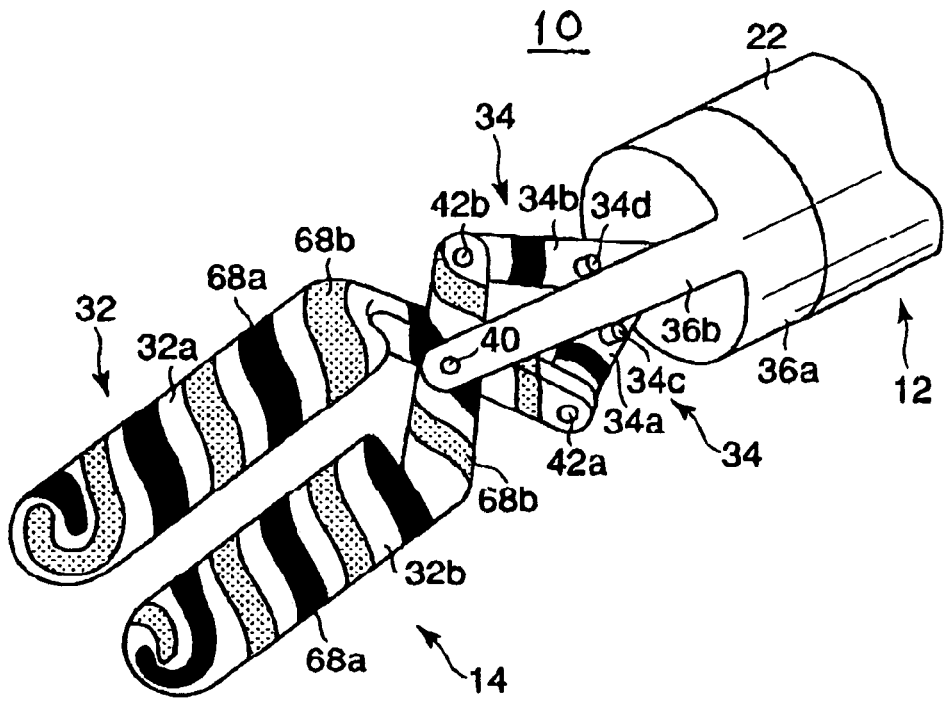
FIG. 10A is a perspective view outlining a treatment member disposed at a tip of a bipolar forceps serving as the high frequency treatment device in a third embodiment of the present invention.
Figure 10B:
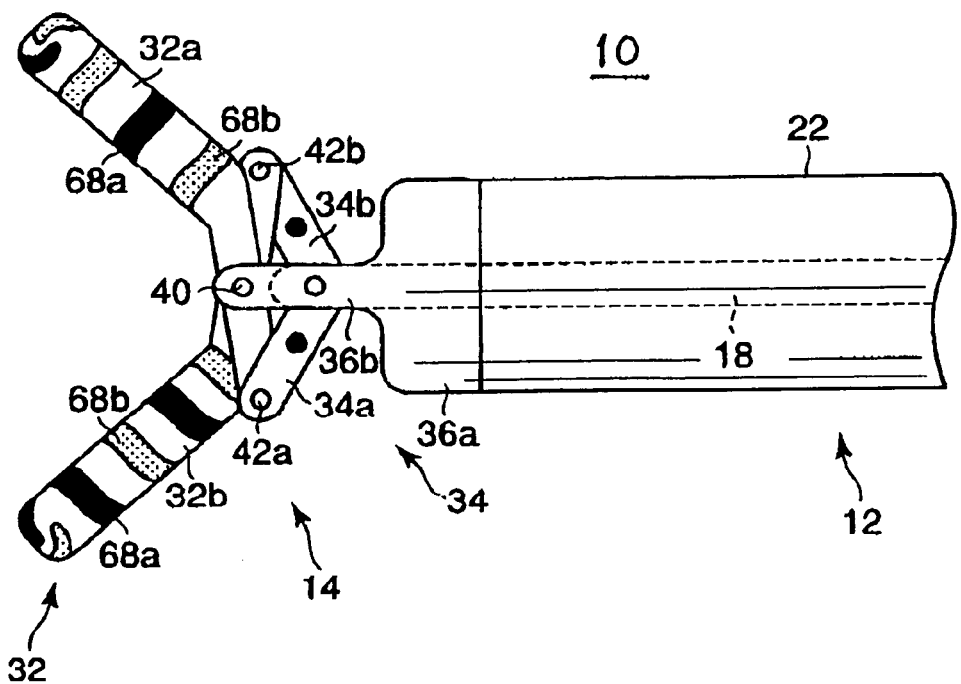
FIG. 10B is a side view outlining the treatment member shown in FIG. 10A, the treatment member being able to take an open position as shown therein.

A gripper 32 shown in FIGS. 10A and 10B has a pair of jaws 32a and 32b, which are made from an eclectically insulative material, such as ceramics, of high heat resistance. That is, in the present embodiment, the jaws 32a and 32b cannot be used as electrodes by themselves.

Instead, as shown in FIGS. 10A and 19B, first and second electrode members 68a and 68b each made from conductive materials are arranged on each of the outer surfaces of the jaws 32a and 32b such that the electrode members are located to have a predetermined distance separation therebetween. That is, the two electrode members 68a and 68b, which are charged with positive and negative polarities, are arranged around each of the jaws 32a and 32b in a spiral and positive/negative-alternate fashion. Both of the electrode members 68a and 68b are eclectically connected with the first and second current-conducting connectors 64 and 64b via the link mechanism 34 and the wire 18, respectively.

The operations of the bipolar forceps 10 will now be described. The operations involving opening and closing the jaws 32a and 32b and the operations involving the closed state of the jaws 32a and 32b are similar to those explained in the first embodiment, thus omitting their detailed explanations. Since the jaws 32a and 32b have the first and second electrode members 68a and 68b spirally disposed on the outer surface of the jaws 32a and 32b along the entire anal range thereof, the jaws 32 and 32b provide the similar operations to those explained in the first embodiment.

Figure 11:
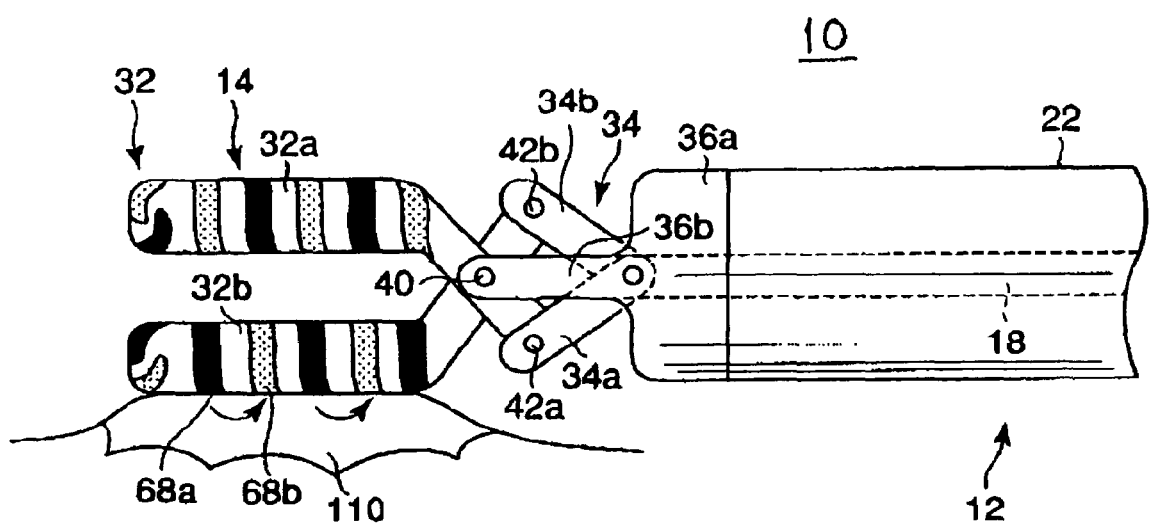
FIG. 11 is the side view outlining the treatment member disposed shown in FIG. 10B, the treatment member being able to take a closed position as shown therein.

As shown in FIG. 11, of the two jaws 32a and 32b, for example, one jaw 32b is made to touch a desired portion of tissue 110 and high frequency vulgate is applied to the first and second electrode members 68a and 68b in the same manner as the foregoing. In response to this, portions of the tissue 110, which along the jaw 32b and each of which resides between the first and second electrode members 68a and 68b, are subjected to high frequency current flow, as shown by arrows in FIG. 11, thus leading to coagulation for blood stanching. That is, only one jaw 32b can be used for blood stanching by simply pressing the jaw 32b to a desired treatment portion of the tissue 110 and applying the high frequency voltage to the jaws 32a and 32b. This is also true of the other jaw 32a.

Figure 12A:
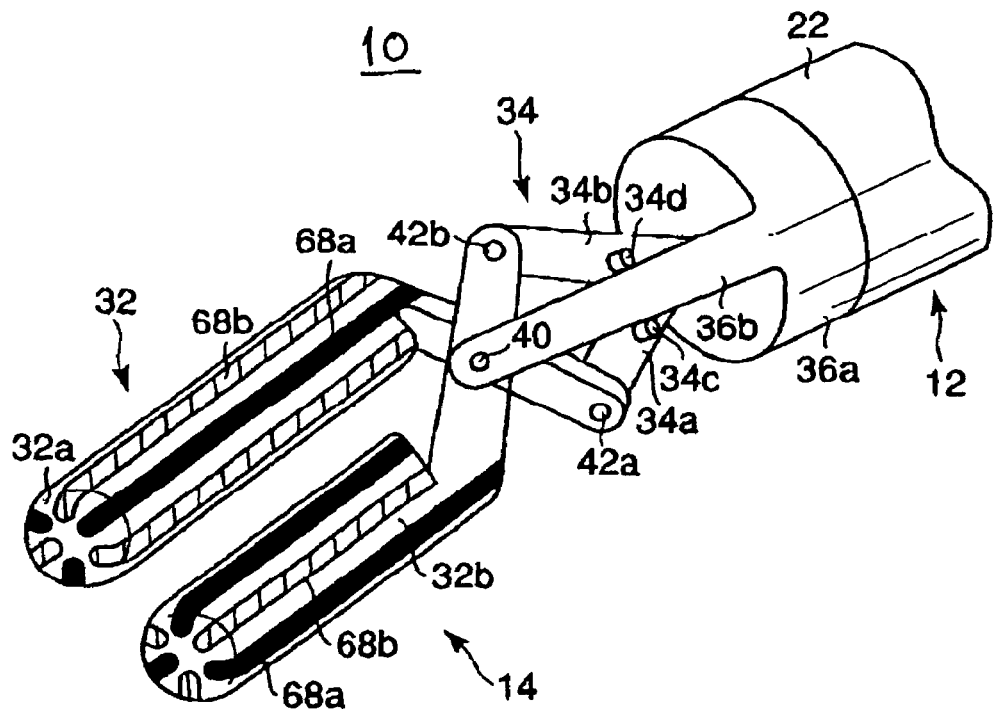
FIG. 12A is a perspective view outlining a treatment member disposed at a tip of a bipolar forceps serving as the high frequency treatment device in a modification of the third embodiment.
Figure 12B:
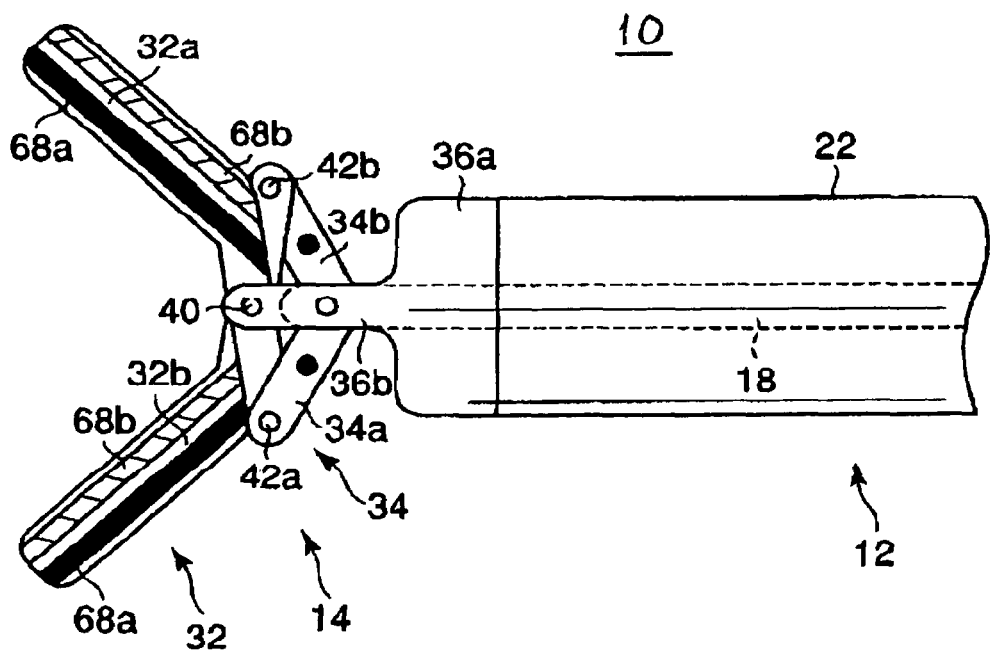
FIG. 12B is a side view outlining the treatment member shown in FIG. 12A, the treatment member being able to take an open position as shown therein.

The spiral electrode members 68a and 68b on each of the jaws 32a and 32b as shown in FIGS. 10A and 10B are not always necessary. An alternative is for example parallel-disposed electrode members 68a and 68b on each of the jaws 32a and 32b as shown in FIGS. 12A and 12B.

Figure 13:
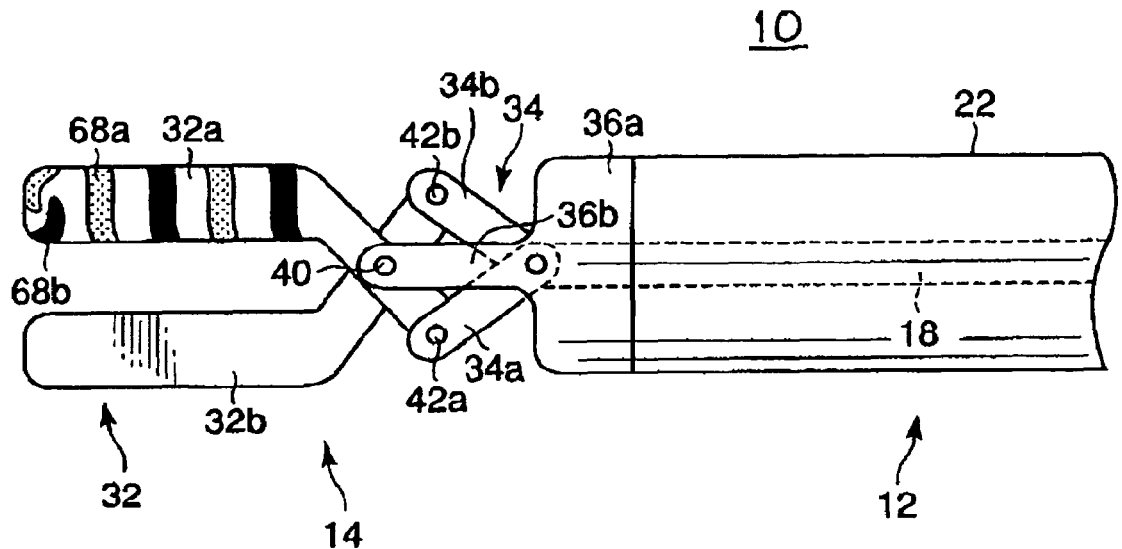
FIG. 13 is a side view outlining a treatment member disposed at a tip of a bipolar forceps serving as the high frequency treatment device in a further modification of the third embodiment.

Another electrode structure can by shown by FIG. 13, in which the first and second electrode members 68a and 68b are disposed on only one 32a of the jaws 32a and 32b, not absolutely necessary for arranging the electrodes on both the jaws 32a and 32b. This type of jaws 32a and 32b are still able to use for both the gripping operations and the touching operations.

Fourth Embodiment

Referring to FIGS. 14A and 14B to FIGS. 16A and 16B, a fourth embodiment of the present invention will now be described. This embodiment relates to a modification of the foregoing third embodiment.

Figure 14A:
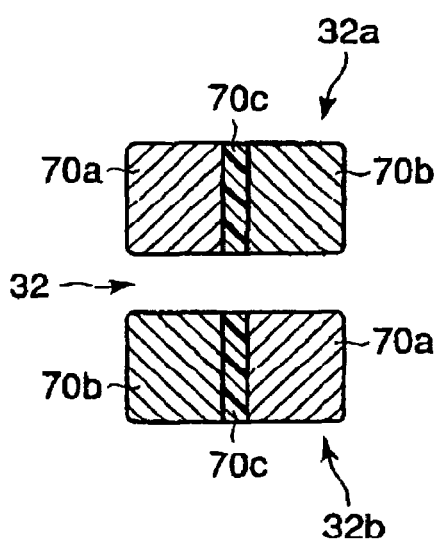
FIG. 14A is a section showing a treatment member disposed at a tip of a bipolar forceps serving as the high frequency treatment device in a fourth embodiment of the present invention.
Figure 14B:
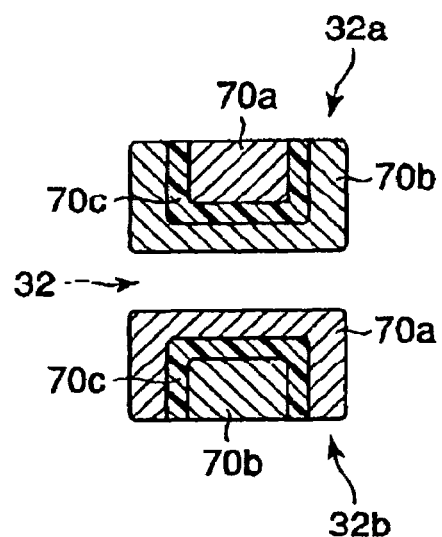
FIG. 14B is a section showing a treatment member disposed at a tip of a bipolar forceps according to a variation of the fourth embodiment.

FIG. 14A shows a front view of jaws 32a and 32b of a gripper 32 used by a bipolar forceps 10 according to the present embodiment. As shown therein, each of the jaws 32a and 32b has first and second electrode members 70a and 70c which are formed into rectangular prisms, respectively, and a plate-like insulator 70c rigidly sandwiched between the electrode members 70a and 70c.

More precisely, of the two jaws 32a and 32b, one of the jaws, 32a, is composed of the first electrode member 70a, insulator 70c, and second electrode member 70c arranged in this order from the left in FIG. 14A. On the other hand, from the left in FIG. 14A, the second electrode member 70b, insulator 70c, and first electrode member 70a are aligned to form the other jaw 32b. The first and second electrode members 70a and 70b receive the high frequency current from positive and negative polarity terminals of the power supply unit, respectively.

The operations of this gripper 32 will now be described in connection with FIGS. 15A and 15B.

Figure 15A:
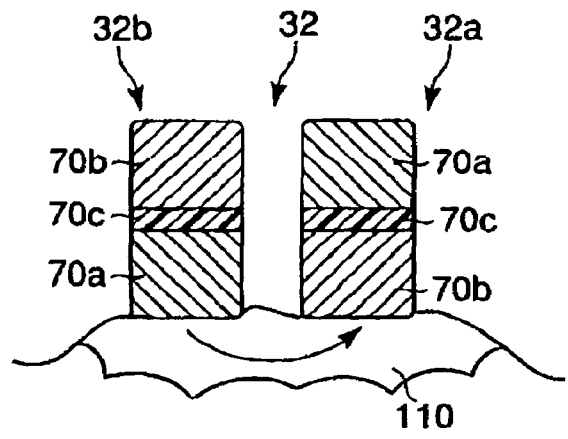
FIG. 15A conceptually shows a state in which a pair of jaws composing the treatment device shown in FIG. 14A is subjected to current supply for treatment of tissue.

As shown in FIG. 15A, side surfaces of the pair of jaws 32a and 32b can be pressed onto a bleeding portion of tissue 110. In this pressed state of the jaws 32a and 32b, the high frequency voltage is applied to the second electrode member 70b of one of the jaws, 32a, and the first electrode member 70a of the other jaws 32b, resulting in that the portion of the tissue 110 touching both the electrode members 70b and 70a undergo the supply of high frequency current, as indicated by an arrow in FIG. 15A. The tissue portion between the pair of jaws 32a and 32b is coagulated to stop bleeding. This operation is also true of the jaws 32a and 32b which have gripped a portion of the tissue 110 for treatment.

Figure 15B:
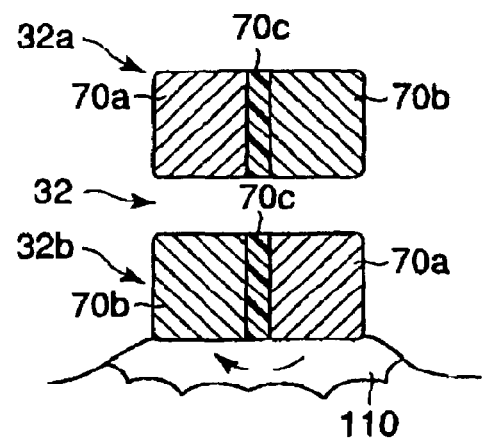
FIG. 15B conceptually shows a state in which one of a pair of jaws composing the treatment device shown in FIG. 14A is subjected to current supply for treatment of tissue.

A further use of the gripper 32 is depicted as shown in FIG. 15B, in which only one of the jaws 32a and 32b is used for treatment. For example, a side of one of the jaws, 32b, is pressed onto a bleeding portion of tissue 110. In this state, the first and second electrode members 70a and 70b on the jaw 32b receives an application of high frequency voltage so that high frequency current passes through a portion residing between the electrode members 70a and 70b. Accordingly, the portion between the electrode members 70a and 70b is coagulated for blood stanching.

Incidentally, the arrangement configurations of the electrode members 70a and 70c and the insulator 70c are not limited to that shown in FIG. 14A. Another example can be shown as in FIG. 14B, wherein each of the jaws 32a and 32b has a U-shaped (in section) insulator 70c. Specifically, one of the jaws, 32a, is composed of a rectangular-prism-like first electrode member 70a, the U-shaped insulator 70c placed to embrace the first electrode member 70a, and a second electrode member 70b U-shaped in section and placed to embrace the insulator 70c, which are all combined rigidly. The other jaw 32b is also composed of the second electrode member 70b, the insulator 70c, and the first electrode member 70a and combined with each other in the same manner as the jaw 32a.

Figure 16A:
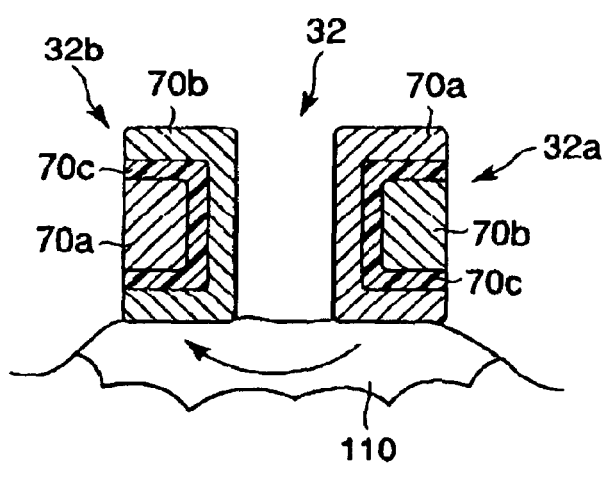
FIG. 16A conceptually shows a state in which a pair of jaws composing the treatment device shown in FIG. 14B is subjected to current supply for treatment of tissue.

In this variation, as illustrated in FIG. 16A, side surfaces of the paired jaws 32a and 32b can be pressed onto a bleeding portion of tissue 110. This allows the tissue portion existing between the first electrode member 70a of one of the jaws, 32a, and the second electrode member 70b of the other jaw 32b to receive the flow of high frequency current. This operation is applicable to the pair of jaws 32a and 32b which has gripped a portion of the tissue 110 for high frequency treatment.

Figure 16B:
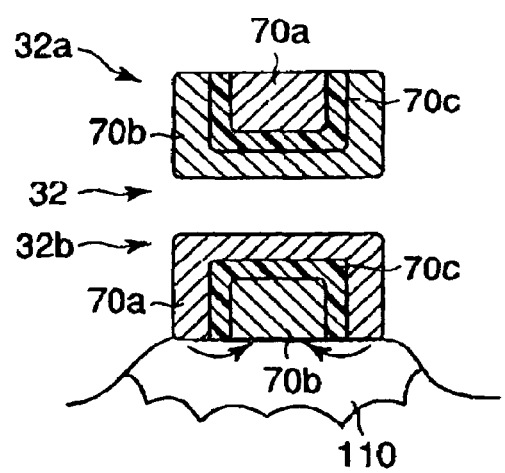
FIG. 16B conceptually shows a state in which one of a pair of jaws composing the treatment device shown in FIG. 14B is subjected to current supply for treatment of tissue

Moreover, as illustrated in FIG. 16B, only one of the jaws, for example, 32b, can be used for high frequency treatment such as blood stanching. That is, it is enough that one of the side surfaces of the jaw 32b, which is opposed to the remaining jaw 32a, is pressed onto a bleeding portion. In this case, a portion residing between the first and second electrode members 70a and 70b undergoes the flow of high frequency current, thus providing the stanching operation at the pressed portion. This is also true of the other jaw 32a.

A further variation is to arrange the electrode members 70a and 70b in only one of the jaws 32a and 32b, not always necessary for arranging them on both the jaws 32a and 32b. Still, in each or only one of the jaws 32a and 32b, a plurality of sets of positive- and negative-polarities electrode members may be formed. This structure of plural sets of electrodes can be achieved by employing two or more insulators arranged in the same manner as the above.

Fifth Embodiment

Figure 17:
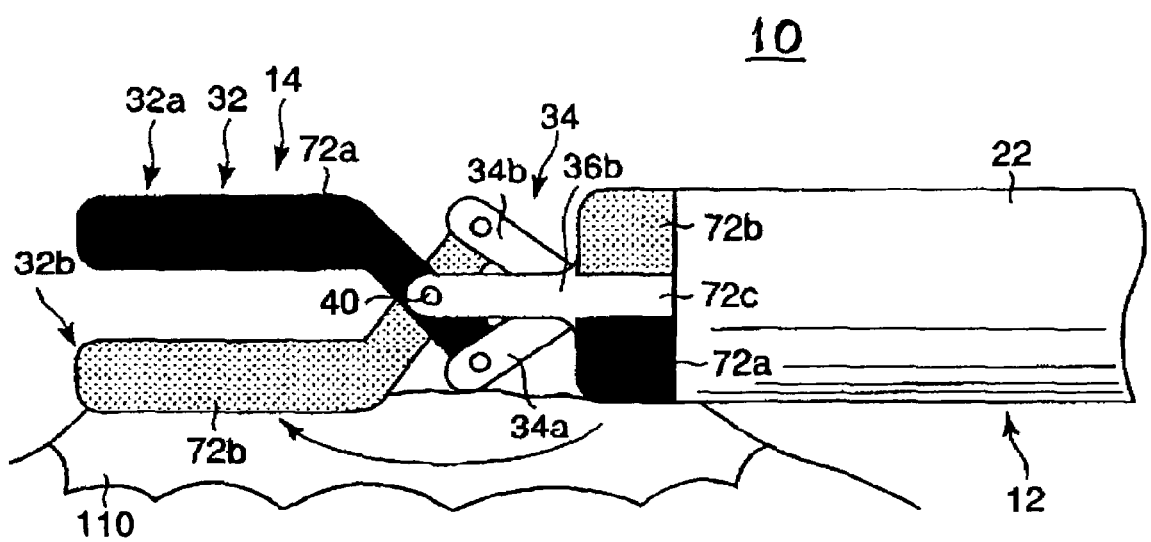
FIG. 17 is a side view outlining a treatment device disposed at a tip member of a bipolar forceps serving as a high frequency treatment device according to a fifth embodiment of the present invention.

Referring to FIG. 17, a fifth embodiment of the present invention will now be described.

As shown in FIG. 17, a bipolar forceps 10 has a tubular tip securing member 36 with a tubular member 36a, which is similar to that explained before and located at the base of the treatment member 14. On the outer surface of the tubular member 36a, formed in the circumferential direction are first and second electrode members 72a and 72b and an insulator 72c separating the electrode members 72a and 72b from one the other. That is, the insulator 72c of a predetermined width prevents the electrode members 72a and 72b from being short-circuited.

The first electrode member 72a of for example positive polarity is also disposed entirely on the outer surface of one of the jaws, 32a, whilst the second electrode member 72b of negative polarity is also disposed entirely on the outer surface of the jaw 32b. Hence both jaws 32a and 32b function as a pair of electrodes, like the jaws 32a and 32b in the first embodiment. In addition, as shown in FIG. 17, the first electrode member 72a on the tubular member 36a and the second electrode member 72b on the other jaw 32b are paired in that they are positionally biased on the same side in a direction perpendicular to the central axis of the insertion member 12. Similarly to this, the second electrode member 72b on the tubular member 36a and the first electrode member 72a on the other jaw 32b are paired.

The first and second electrode members 72a and 72b are electrically connected to the first and second current-conducting connectors 64a and 64b, respectively, within the sheath 22 of the insertion member 12 via the wire 18.

The operations of the bipolar forceps 10 according to the present embodiment will now be described.

For example, in cases where one of the jaws, 32b, is pressed onto a portion of tissue 110 for blood stanching, the paired first electrode member 72a on the tubular member 36a is pressed together onto the portion. An application of high frequency voltage to the first and second electrode members 72a and 72b thus pressed allows high frequency current to flow between the jaw 32b (second electrode member 72b) and the first electrode member 72a on the tubular member 36a, as depicted by an arrow in FIG. 17. This will cause coagulation at the desired portion for blood stanching.

Hence the present embodiment provides an advantage, in addition to those gained in the first embodiment. That is, in pressing the jaws 32a and 42b for blood stanching, either of the positionally biased two pairs selected from the jaws 32a and 32b and the electrodes 72 and 72b is simply pressed onto a bleeding portion of tissue 110. An example is shown in FIG. 17. In such a pressed state, the electrode members 72a and 72b is subject to the supply of high frequency current. This is a simple operation for blood stanching, shortening a time for the overall treatment operations.

In addition, the positions and shapes of the first and second electrodes 72 and 72b are not limited to that shown in FIG. 17. Further, the first electrode member 72a and the second electrode member 72b are not limited to one in number, respectively. Plural mutually-opposite-polarity electrodes can be placed on the jaw 32a (32b) at intervals, for example.

Sixth Embodiment

Referring to FIGS. 18A and 1813 to 21A and 21B, a sixth embodiment of the present invention will now be described.

Figure 18A:
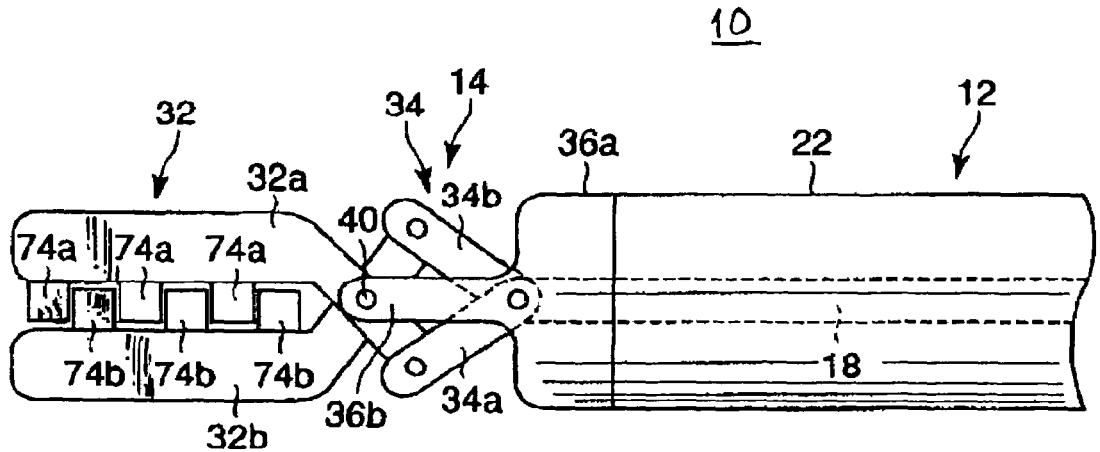
FIG. 18A is a side view outlining a treatment device disposed at a tip member of a bipolar forceps serving as a high frequency treatment device according to a sixth embodiment of the present invention, the treatment device being depicted in its closed attitude.
Figure 18B:
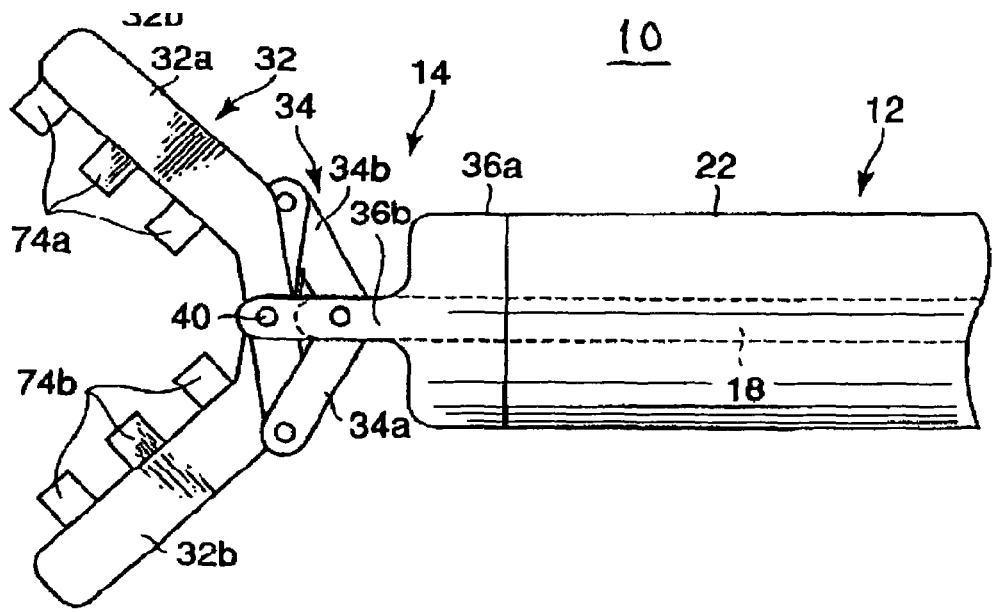
FIG. 18B is the side view of the treatment device shown in FIG. 18A, the treatment device being depicted in its open attitude.

FIGS. 18A and 18B show a gripper of a bipolar forceps 10 according to the present embodiment, in which the gripper 32 comprises a pair of jaws 32a and 32b made from conductive materials, like the first embodiment. In other words, the jaws 32a and 32b function as electrodes by themselves. The jaws 32a and 32b are electrically connected to the first and second current-conducting connectors 64a and 64b via the wire 18.

As illustrated in FIGS. 18A and 18B, on each of the gripping surfaces 38a and 38b of the jaws 32a and 32b, a plurality of insulators 74a (74b) are rigidly built at intervals along the longitudinal (axial) direction of the gripper 32. Each of the insulators 74a and 75b is formed into, for example, a cubic or a cuboid in the present embodiment, but this is not a decisive list. Any shapes such as hemisphere shape, truncated cone shape, and triangular pyramid shape can be adopted as the insulators 74a and 74b. It is preferable that the number of insulators 74a (74b) is one to five in number in the axial direction of each jaw in order to keep a sufficient gripping force. The insulators 74a and 74b are made from a highly insulative and heat-resistive material, for example, selected from a group consisting of ceramic material, cycloolefin resin, norbornane resin, polyether ether ketone, polyimide, polyamide, and polysufone.

As shown in FIGS. 18A and 18B, the dimensional configurations are given to the jaws 32a and 32b such that, when the jaws 32a and 32b are closed at full, the insulators 74a and 74b on the mutually opposed gripping surfaces 38a and 38b do not interfere with each other. Concretely, the insulators 74a and 75b are located alternately along the longitudinal direction of the gripper 32 when the closing operations of the jaws 32a and 32b are completed and a gap of slight distance is formed between the mutually adjacent insulators 74a and 74b on both the jaws 32a and 32b in the longitudinal direction.

The operations of the bipolar forceps 10 according to the present embodiment will now be described.

The description will given on the assumption that the pair of jaws 32a and 32b are used to grip a portion of tissue 110 to stop bleeding from the portion.

Figure 19:
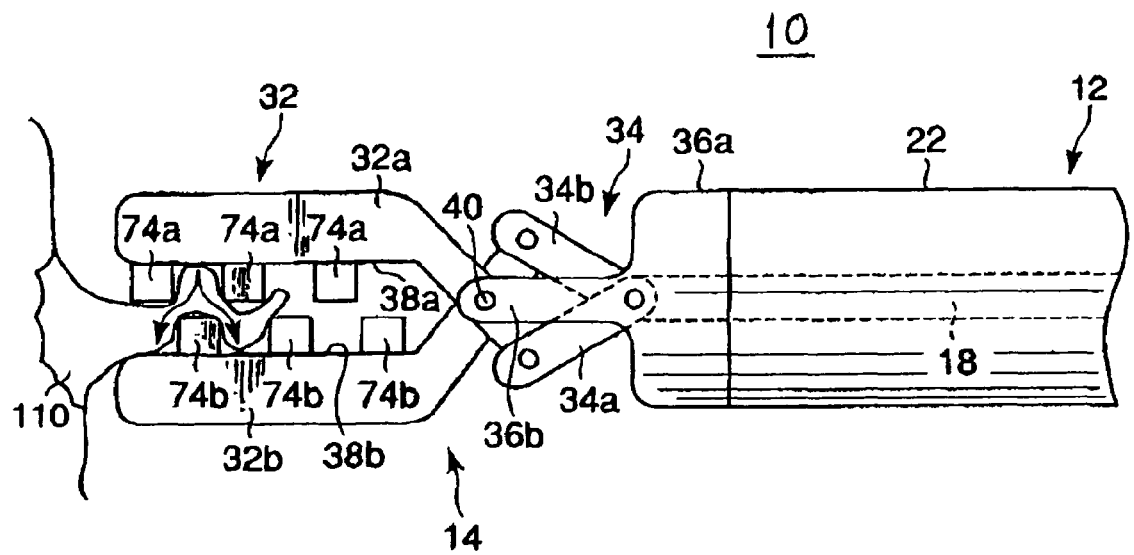
FIG. 19 is the side view showing the treatment device shown in FIG. 18A, the treatment device being depicted with its jaws gripping tissue.

In this operation, as shown in FIG. 19, the portion of the tissue 110 is gripped between the gripping surfaces 38a and 38b. In detail, the tissue portion 10 is pressed onto the gripping surface 38b of one of the jaws, 32b, by the insulators 74a of the other jaw 32a and pressed onto the gripping surface 38a of the jaw 32a by the insulators 74b on the jaw 32b. In response to an application of high frequency voltage to the jaws 32a and 32b, high frequency current flows through the gripped tissue portion, as shown by arrows in FIG. 19. Hence, the gripped tissue portion 110 coagulates to stop bleeding therefrom.

Figure 20A:
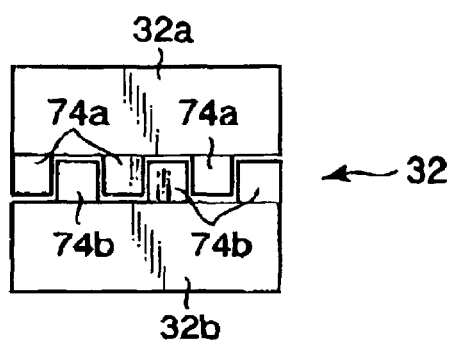
FIG. 20A is a frontal view showing a treatment device of a bipolar forceps according to a modification of the sixth embodiment, the treatment device shown therein taking its closed position.
Figure 20B:
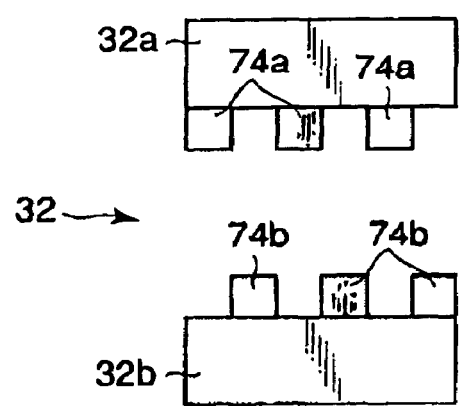
FIG. 20B is the frontal view showing the treatment device of the bipolar forceps shown in FIG. 20B, the treatment device shown therein taking its open position.

A variation of the foregoing is shown in FIGS. 20A and 20B, which pictorially depict front views of the jaws 32a and 32b composing the gripper 32. As shown therein, it is preferred that a plurality of rows of the insulators 74a (74b) are arranged in parallel in the longitudinal (axial) direction of the gripper 32, not limited to the arrangement in which each row of the insulators 74a (74b) is aligned in the direction perpendicular to the longitudinal direction. The axial length of each insulator 74a (74b) is 0.5 to 20 mm and set to an amount not to protrude from the jaws 32a and 32b.

According to the present embodiment, unlike the bipolar forceps 10 explained in the first embodiment, even if the jaws 32a and 32b are closed at full, there exist the insulators 74a and 74b between the jaws 32a and 32b. Therefore, stoppers to limit the rotations of the jaws 32a and 32b, such as stoppers 34c and 34d in FIGS. 3A and 3B, are not required any more.

Seventh Embodiment

Figure 21A:
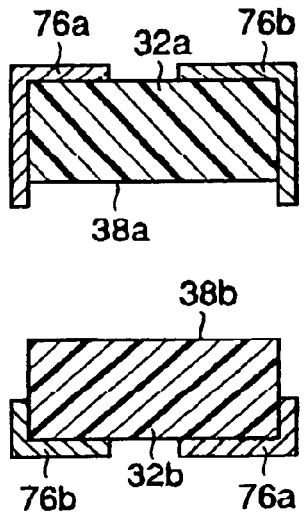
FIG. 21A is a frontal view showing a treatment device of a bipolar forceps serving as the high frequency treatment device according to a seventh embodiment of the present invention, the treatment device shown therein taking its open position.
Figure 21B:
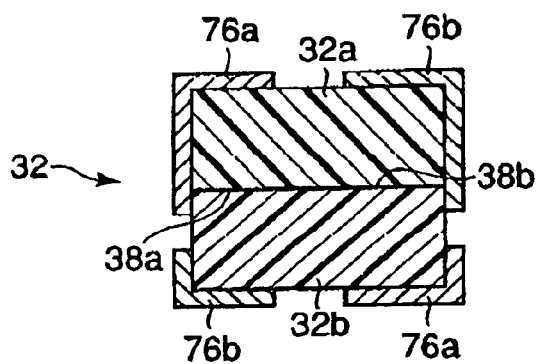
FIG. 21B is the frontal view of the treatment device shown in FIG. 21A, the treatment device shown therein taking its closed position.
Figure 22:
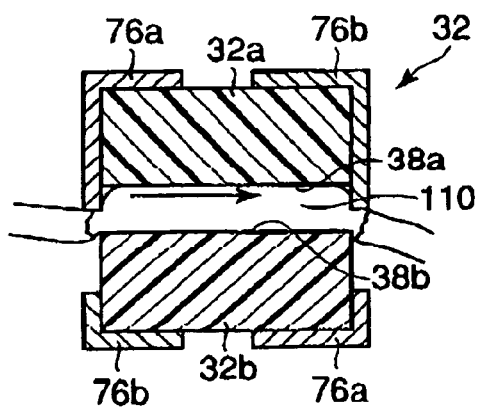
FIG. 22 is the frontal view of the treatment device shown in FIGS. 21A and 21B, the treatment device shown therein gripping tissue.

Referring to FIGS. 21A, 21B and 22, a seventh embodiment of the present invention will now be described. This embodiment provides a modified example from the electrode configurations shown in the sixth embodiment in which the stoppers 34c and 34d explained in FIGS. 3A and 3B are unnecessary.

A bipolar forceps 10 according to the present embodiment has a gripper 32 shown in FIGS. 21A and 21B. The gripper 32 has jaws 32a and 32b made from insulative materials. Gripping surfaces 38a and 38b formed on the jaws 32a and 32b can be contacted to each other, as shown in FIG. 21B. On both corner surfaces of each of the jaws 32a and 32b, first and second L-shaped electrode members 76a and 76b are secured with a predetermined interval therebetween.

To be specific, on one of the jaws, 32a, the first and second L-shaped electrode members 76a and 76b are secured to cover part of the upper surface and a side surface and to protrude from the lower end of the jaw 32a by a predetermined length, respectively, as shown in FIG. 21A. On the upper surface in the FIG. 21A, the two electrode members 76a and 76b are separated from each other by a predetermined length.

On the other hand, on the other jaw 32b, the first and second L-shaped electrode members 76a and 76b are secured to cover part of the lower surface and part of a side surface of the jaw 32b, respectively, as shown in FIG. 21A. On the lower surface shown in the FIG. 21A, the two electrode members 76a and 76b are separated a predetermined length from each other. The electrode members 76a and 76b receive an application of high frequency voltage of positive and negative polarities, respectively.

As shown in FIG. 21B, when the pair of jaws 32a and 32b are closed completely, the lower ends of the first and second electrode members 76a and 76b disposed on one of the jaws, 32a, are made to touch both side surfaces of the other jaw 32b. In this closed state of both the jaws 32a and 32b, the first and second electrode members 76a and 76b on the jaw 32b and the first and second electrode members 76a and 76b on the jaw 32a are separated from each other.

As long as the foregoing conditions illustrated in FIGS. 21A and 21B are met, the first and second electrode members 76a and 76b can be formed into any shapes, not limited to those expressed by FIGS. 21A and 21B. Though an arbitrary number of electrode members are available for each of the first and second electrode members 76a and 76b, it is preferable to dispose two to six electrode members are disposed along the longitudinal direction of the jaws 32a and 32b when taking the arrangement areas on the jaws into account.

The operations of the bipolar biceps 10 according to the present embodiment will now be described.

The pair of jaws 32a and 32b can also grip a portion of tissue 110 to stop bleeding from the portion.

This gripping operation is illustrated in FIG. 22. When this gripping action is completed, high frequency voltage is applied to the first and second electrode members 76a and 76b on each of the jaws 32a and 32b so that high frequency current flows between the jaws 32a and 32b through the portion of the tissue. Hence the gripped portion is coagulated to stop bleeding.

Although not shown, one-side surfaces of the jaws 32a and 32b can be touched to the tissue 110 to apply high frequency voltage to the first and second electrode members 76a and 76b. As a result, high frequency current flows between the paired first and second electrode members 76a and 76b on the paired jaws 32a and 32b, with a touched tissue portion coagulated for blood stanching.

In the present embodiment, it is not required to limit the angles of the jaws 32a and 32b in having the tissue 110 gripped for stanching. Thus a stronger pressing force can therefore be applied to the tissue 110 when gripping it, applying a more effective press to the tissue 110 with the jaws 32a and 32b for blood stanching.

Eighth Embodiment

Referring to FIGS. 23A, 23B, 24A and 24B, an eighth embodiment of the present invention will now be described.

Figure 23A:
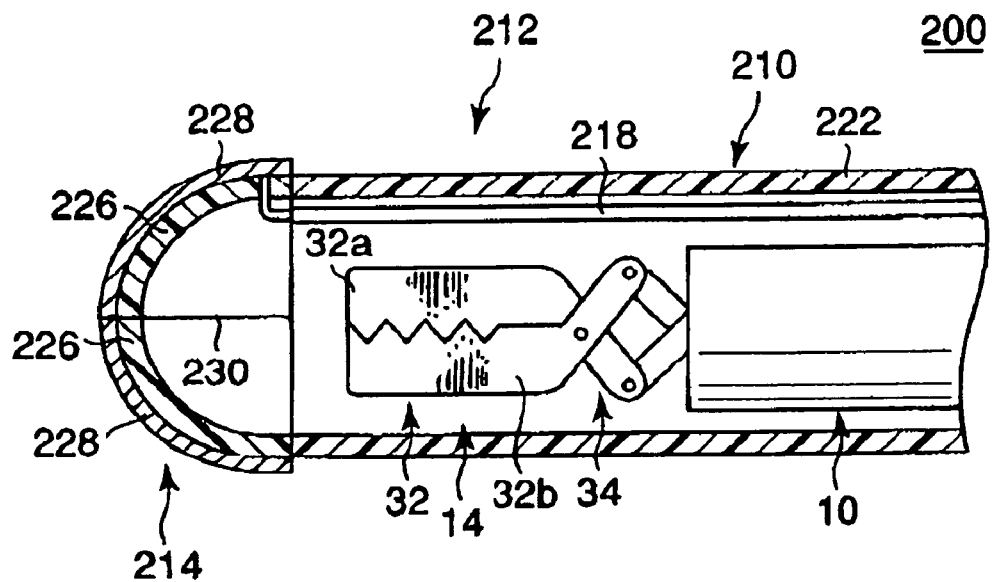
FIG. 23A is a partly sectioned view showing a tip of the high frequency treatment device according to an eighth embodiment of the present invention.

A high frequency treatment device according to the present embodiment, when it is used, is inserted into the insertion channel 102 of for example the endoscope 100 as shown in FIG. 1. As shown in FIG. 23A, a high frequency treatment device 200 according to the present embodiment is provided with a monopolar stanching device (a coagulating device or a coagulater) 210 and a bipolar forceps (high frequency gripping forceps) 10 placed within the monopolar stanching device 210. Of these devices, the bipolar forceps 10 by be, by way of example, identical in configurations to those explained in the first to seventh embodiments. Particularly in the present embodiment, the bipolar forceps 10 is identical to that in the first embodiment.

As shown in FIGS. 23A and 233, the monopolar stanching device 210 is provided with a thin and flexible insertion member 212, a treatment member 214 secured to the tip of the insertion member 212, and a current-supply connector 216 secured to the base of the insertion member 212.

In the monopolar stanching device 210, the insertion member 212 is provided with a sheath 222 rotatable against the treatment member 214. The sheath 222 is made from a resin material that exhibits an excellent flexibility. The sheath 222 may however be formed from a metal-made flexible coil, not limited to the resin materials. The sheath 222 has an inner diameter to form an inner tubular space through which the treatment member 12 and insertion member 14 of the bipolar forceps 10 are inserted smoothly. The outer diameter of the sheath 222 is 1.5 to 6 mm. Particularly it is preferable if the outer diameter is 2.2-3.5 mm. In the inner bore of this sheath 222, a current-supply cable 218 is arranged along the axial direction of the sheath 222.

Figure 23B:
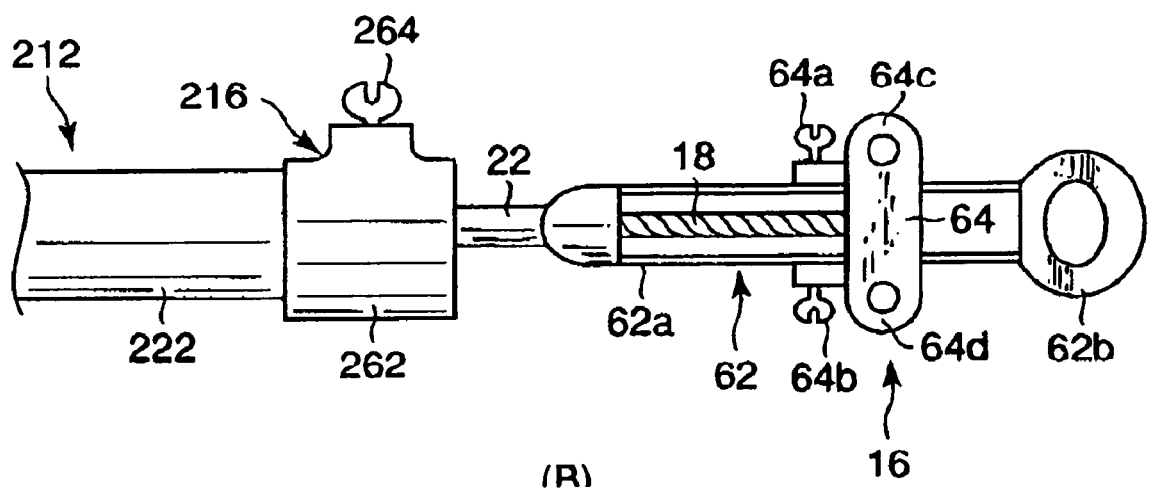
FIG. 23B is a partial side view showing a base of the high frequency treatment device shown in FIG. 23B.

As shown in FIG. 23B, the current-supply connector 216 of the monopolar stanching device 210 is a tubular connecter body 262 and a terminal 264 secured on this connector body 262. The connector body 262 has an inner hole connecting both axial ends and the diameter of the hole is set to an amount permitting the treatment member 14 and insertion member 12 of the bipolar forceps 10 to be inserted smoothly. The terminal 264 is electrically connected with an end of the current-supply cable 218.

As shown in FIG. 23A, the treatment member 214 is provided with a hemispheric valve 226 that has sufficient elasticity and an electrode 228 being formed from conductive material, such as elastomeric resin, and covering the valve 226. Each of the valve 226 and the electrode 228 is divided by slits 230 into plural segments and formed to open and close.

On the outer surface of each of the segments of the valve 226, each segment of the electrode 228, which is the same in shape as each segment of the valve 226, is affixed. The tip of the current-supply cable 218 is electrically coupled with the electrode 228. That is, the current-supply cable 218 electrically connects the electrode 228 and the terminal 264 of the current-supply connector 216.

By the way, it is not always necessary that the segments of the electrode 228 are affixed on all the segments of the valve 226, but is enough if only one electrode segment is affixed on any segment of the valve 226. In addition, the number of slits 230 of the valve 226, that is, the number of segments thereof, is arbitrary.

The operations of the high frequency treatment device 200 according to the present embodiment will now be described.

First, the bipolar forceps 10, which is part of the device 200, will now be explained.

Current-supply cables are used to connect the current-supply connectors 64a, 64b and 264 of both the monopolar stanching device 210 and the bipolar forceps 10 to high frequency power supply units (not shown), respectively.

Figure 24A:
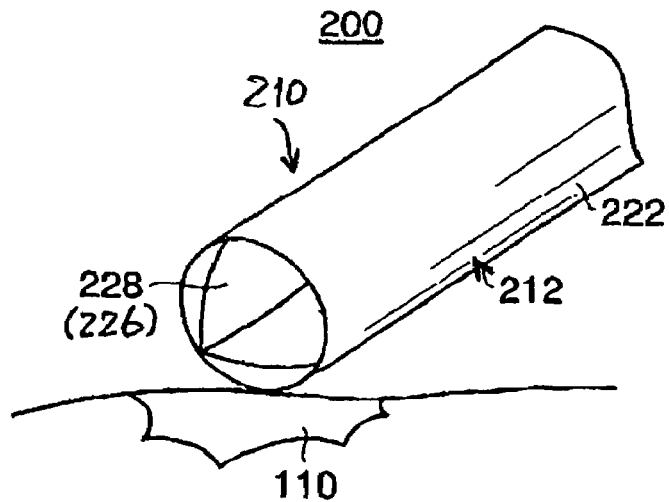
FIG. 24A is a perspective view outlining the high frequency treatment device shown in FIG. 23A, the high frequency treatment device having a monopolar blood-stanching device whose electrodes are pressed onto tissue for treatment.

The high frequency treatment device 200 is inserted into the insertion channel of the endoscope 100 so as to make the tip of the device 200 approach a portion of tissue 110 to be treated, in which the treatment member 14 and insertion member 12 of the bipolar forceps 10 are inserted into the insertion member 212 (sheath 222) of the monopolar stanching device 210 through the tip thereof. As shown in FIG. 24A, the tip of the high frequency treatment device 200 is served by the treatment member 214 of the monopolar stanching device 210.

Figure 24B:
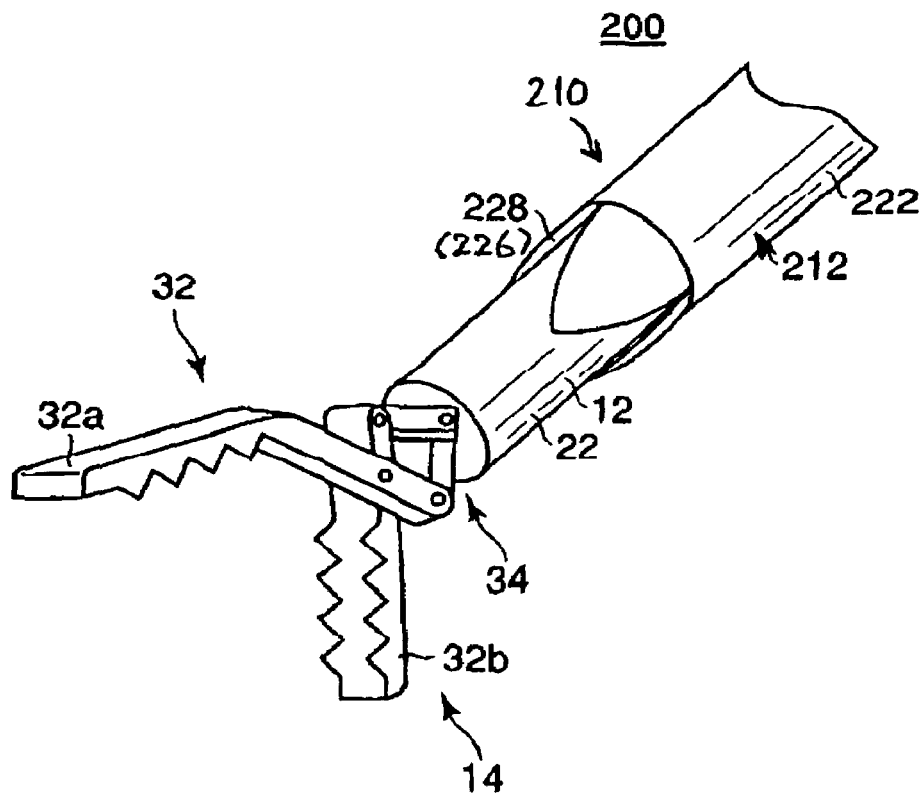
FIG. 24B is a perspective view explaining the high frequency treatment device with the monopolar blood-stanching device from which a bipolar forceps is made to jut out to open a treatment member of the forceps.

As shown in this state shown in FIG. 24A, the bipolar forceps 10 is operated to advance toward the tip of the monopolar stanching device 210 within this device 210. Then, as shown in FIG. 24B, from the tip of the monopolar stanching device 210, the treatment device 14 of the bipolar forceps 10 is pushed out to open the valve 226 and electrode 228 of the outer device 210. In this pushing operation, since the valve 226 has elasticity, the segments of the valve 226 can be pushed aside to form an opening in an easy manner. Thus the treatment member 14 of the bipolar forceps 10 can protrude from the outer device 210.

Accordingly, like the operations in the first embodiment, the treatment member 14 is able to grip a portion of tissue 110 for blood stanching using the current-supplied jaws 32a and 32b.

In contrast, the monopolar stanching device 210 can be used for blood stanching by having the device 210 itself pressed onto a portion of tissue.

In the similar manner to the bipolar forceps 10, the high frequency treatment device 200, in which the bipolar forceps 10 is contained within the monopolar stanching device 210, is operated so that its tip approaches a bleeding portion of tissue 110, as shown in FIG. 24A. And the electrode 228 on the tip of the monopolar stanching device 210 is touched to the bleeding portion and receives an application of high 6 frequency voltage from the high frequency power supply unit. This application allows high frequency current to flow through the electrode and bleeding portion, with the blooding portion coagulated for performing blood stanching.

A variation according to this embodiment is to replace the bipolar forceps 10 with a monopolar forceps and to replace the monopolar stanching device 210 with a bipolar stanching device.

Ninth Embodiment

Figure 25:
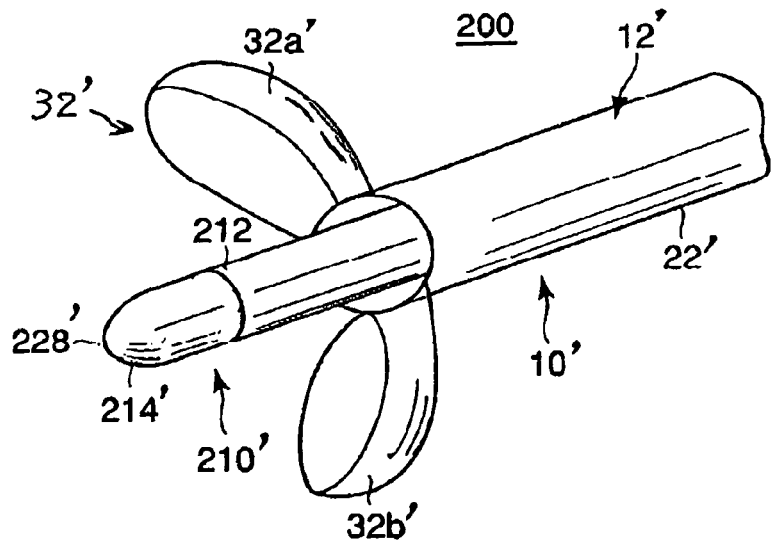
FIG. 25 is a perspective view outlining a high frequency treatment device according to a ninth embodiment of the present invention, the high frequency treatment device shown therein being provided with a bipolar forceps from which a monopolar blood-stanching device with electrodes is made to jut out.
Figure 26:
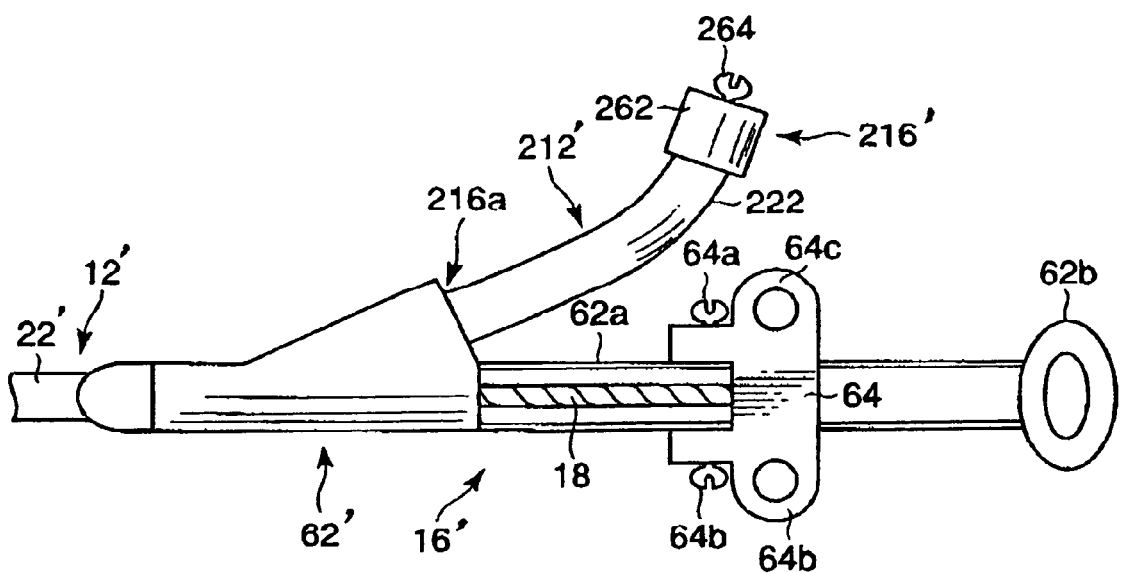
FIG. 26 is a side view outlining a base of the high frequency treatment device according to the ninth embodiment.

Referring to FIGS. 25 and 26, a ninth embodiment of the present invention will now be described, which is modified from the constructions in the eighth embodiment.

As shown in FIG. 25, a high frequency treatment device 200 according to the present embodiment has also a double-device structure and is provided with a bipolar forceps 10, arranged as an outer device and a monopolar stanching device 210' arranged within an insertion member 12' of the bipolar forceps 10'. The insertion member 12' of the forceps 10' has a tubular through-hole sufficient therein for insertion of an insertion member 212' of the monopolar stanching device 210'.

As shown in FIG. 26, the bipolar forceps 10' has a handle 16' with an operating main body 62', which is similar to the ones of the foregoing embodiments. In the operations main body 62, an insertion channel 216a is formed to accept the insertion of a treatment member 214' and an insertion member 212' of the monopolar stanching device 210'. This insertion channel 216a has a diameter of which amount is appropriate for a smooth insertion of the insertion member 212'.

This high frequency treatment device 200 will now be explained in terms of its operations.

The bipolar forceps 10', functioning as part of the device 200, has the capability of stopping bleeding. Cables are used to connect both the monopolar stanching device 210' and the bipolar forceps 10' to the high frequency power supply unit.

With the monopolar stanching device 210' inserted into the insertion channel 216a of the handle 16' of the bipolar forceps 10', the high frequency treatment device 200, that is, the bipolar forceps 10', is operated to make its tip approach a bleeding portion of tissue through the insertion channel 102 of the endoscope 100.

In the similar manner to the gripping operation explained in the first embodiment, jaws 32a' and 32b' of the bipolar forceps 10' are then driven to grip the bleeding portion and subjected to high frequency current supply.

Further, making the monopolar stanching device 210' touch a bleeding portion of tissue leads to blood stanching.

Similarly to the blood stanching carried out with the bipolar forceps 10', the device 200 is operated to make its tip approach a bleeding portion of tissue. Then a gripper 32' of the bipolar forceps 10', which consists of the jaws 32a' and 32b', is opened by driving the jaws 32a' and 32b' so that its tips are rotated in the mutually different directions. After completing this open as shown in FIG. 25, the monopolar stanching device 210' is moved to protrude its treatment member 214' from the tip of the insertion member 12' of the outer forceps 10'.

An electrode 228' on the tip of the monopolar stanching 210' is then pressed to a bleeding portion of tissue. Thus the blood stanching is achieved at the portion, like the foregoing.

Therefore, in the present embodiment, the gripper 32' of the bipolar forceps 10' can grip tissue to perform blood stanching with the aid of high frequency current. Further, any portion of the treatment member 214' of the monopolar stanching device 210' can be pressed to a bleeding portion of tissue for stanching. Thus both of these stanching ways can be used selectively depending on various bleeding conditions. That is, the single high frequency treatment device 200 has the two high frequency treatment functions, thus being convenient and efficient for the stanching operations.

The present invention may be embodied in other specific forms without departing from the spirit or essential characteristics thereof. The present embodiments and modifications are therefore to be considered in all respects as illustrative and not restrictive, the scope of the present invention being indicated by the appended claims rather than by the foregoing description and all changes which come within the meaning and range of equivalency of the claims are therefore intended to be embraced therein.

What is claimed is:

1. A high frequency treatment device comprising:
   a flexible insertion member;
   a pair of jaws, each jaw oriented in a longitudinal direction, and each jaw of the pair being made of an electrically conductive material so as to have an electrode function along an entire region of each jaw of the pair in the longitudinal direction, and each jaw of the pair having a gripping surface, a front surface, and a side surface, the gripping surface being for a coagulation operation applied to an object and the front and side surfaces being for a blood stanching operation applied to the object, each jaw serving as one of positive and negative electrodes to which the high frequency voltage is applied;
   a link member holding the pair of jaws to be opened and closed in a direction allowing the gripping surfaces of the jaws to be opposed to each other, linking the pair of jaws to a tip of the insertion member in a condition in which an electrical insulation between the jaws is kept, and including two links respectively coupled with the pair of jaws;
   a short-circuit preventing member preventing an electrical short circuit between the pair of jaws when the pair of jaws are closed to each other, wherein the short-circuit preventing member is provided with a limiting member to limit a rotation range of each jaw in a closing direction along which each jaw of the pair is rotated, the rotation range being set to secure a gap of predetermined length between the pair of jaws in a fully closed state, wherein the limiting member includes two pins each secured to each of the two links and configured to interfere with an arm secured to the insertion member to limit the rotation range of each jaw of the pair in the closing direction;
   a power line being disposed through the insertion member and applying a high frequency voltage to the pair of jaws via the link member to cause a high frequency current to flow through the pair of jaws; and an operation wire being disposed through the insertion member and transmitting open/close movements to the pair of jaws via the link member.

2. The device according to claim 1, wherein the link member includes two jaw arms intervening between bases of each jaw of the pair and the two links, respectively, the jaw arms having an electrically insulative outer surface.

3. The device according to claim 1, wherein the gripping surface of each jaw of the pair has irregularities, respectively.

4. The device according to claim 1, wherein the front surface of each jaw of the pair is one in number and the side surface of each jaw of the pair comprises two side surfaces and each of the front and side surfaces is adjacent to the gripping surface.

5. The device according to claim 4, wherein the two side surfaces of each jaw of the pair are opposed to each other and located back to back in a side direction of each jaw.

* * * * *